15 US006353099B1

(12) United States Patent
DeLaszlo et al.

(10) Patent No.: US 6,353,099 B1
(45) Date of Patent: Mar. 5, 2002

(54) SUBSTITUTED UREAS AS CELL ADHESION INHIBITORS

(75) Inventors: Stephen E. DeLaszlo, Rumson; William K. Hagmann, Westfield; Theodore M. Kamenecka, Atlantic Highlands, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/641,408

(22) Filed: Aug. 17, 2000

Related U.S. Application Data

(60) Provisional application No. 60/150,055, filed on Aug. 20, 1999.

(51) Int. Cl.[7] .................... C07D 267/02; C07D 295/00; C07D 211/00; C07D 211/78; C07D 207/00
(52) U.S. Cl. .................. 540/490; 540/582; 546/15; 546/197; 546/286; 548/535; 548/579; 562/507; 560/155
(58) Field of Search ............................... 560/125, 169; 562/507, 560; 546/15, 184, 400, 532; 549/1; 540/490, 582

(56) References Cited

U.S. PATENT DOCUMENTS

| 4,415,566 A | * | 11/1983 | Wetzel et al. |
| 5,869,489 A | * | 2/1999 | Shah et al. |
| 6,069,163 A | * | 5/2000 | Delaszlo |

FOREIGN PATENT DOCUMENTS

| EP | 0798291 A1 | * | 1/1997 |
| WO | WO 99/36393 | | 7/1999 |

OTHER PUBLICATIONS

Chong et al., Jun. 1999. Solid phase urea synthesis: An efficient and direct conversion of Fmoc–protected amines to ureas. Tetrahedron letters 40(24), pp. 4501–4504.*
CAPLUS abstract 1974:133785 (1974), Davidovich et al. Amino acid derivatives of phenylalkylamines. Izv. Akad. Nauk SSSR, Ser. Khim (1), 170–4.*

* cited by examiner

*Primary Examiner*—Paul J. Killos
*Assistant Examiner*—Mahreen Chaudhry
(74) *Attorney, Agent, or Firm*—Mollie M. Yang; David L. Rose

(57) ABSTRACT

Compounds of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of AIDS-related dementia, allergic conjunctivitis, allergic rhinitis, Alzheimer's disease, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, multiple myeloma, myocarditis, organ transplantation, psoriasis, pulmonary fibrosis, restenosis, retinitis, rheumatoid arthritis, septic arthritis, stroke, tumor metastasis, uveititis, and type I diabetes.

7 Claims, No Drawings

US 6,353,099 B1

SUBSTITUTED UREAS AS CELL ADHESION INHIBITORS

CROSS-REFERENCE TO RELATED APPLICATIONS

This application is a non-provisional application related to U.S. Application Ser. No. 60/150,055 filed on Aug. 20, 1999 priority of which is claimed hereunder.

SUMMARY OF THE INVENTION

The compounds of the present invention are antagonists of the VLA-4 integrin ("very late antigen-4"; CD49d/CD29; or $\alpha_4\beta_1$), the $\alpha 4\beta 7$ integrin (LPAM-1 and $\alpha_4\beta_p$), and/or the $\alpha 9\beta 1$ integrin, thereby blocking the binding of VLA-4 to its various ligands, such as VCAM-1 and regions of fibronectin, $\alpha 4\beta 7$ to its various ligands, such as MadCAM-1, VCAM-1 and fibronectin, and /or $\alpha 9\beta 1$ to its various ligands, such as tenascin, osteopontin and VCAM-1. Thus, these antagonists are useful in inhibiting cell adhesion processes including cell activation, migration, proliferation and differentiation. These antagonists are useful in the treatment, prevention and suppression of diseases mediated by VLA-4, $\alpha 4\beta 7$-, and/or $\alpha 9\beta 1$-binding and cell adhesion and activation, such as AIDS-related dementia, allergic conjunctivitis, allergic rhinitis, Alzheimer's disease, aortic stenosis, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, myocarditis, organ transplantation, psoriasis, restenosis, retinitis, rheumatoid arthritis, septic arthritis, stroke, tumor metastasis, type I diabetes, vascular occlusion following angioplasty.

BACKGROUND OF THE INVENTION

The present invention relates to substituted urea derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of a and b heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, NY, 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of of these cell types (see M. E. Hemler, "VLA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to proinflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, N.Y., 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al.,J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

The $\alpha 9\beta 1$ integrin is found on airway smooth muscle cells, non-intestinal epithelial cells (see Palmer et al.,J. Cell Biol., 123, 1289 (1993)), and neutrophils, and, less so, on hepatocytes and basal keratinocytes (see Yokosaki et al., J. Biol. Chem., 269, 24144 (1994)). Neutrophils, in particular, are intimately involved in acute inflammatory repsonses. Attenuation of neutrophil involvement and/or activation would have the effect of lessening the inflammation. Thus, inhibition of $\alpha 9\beta 1$ binding to its respective ligands would be expected to have a positive effect in the treatment of acute inflammatory conditions.

Neutralizing anti-$\alpha 4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha 4$ integrin throughout active experimental allergic encfephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." *J. Clin. Invest.* 93, 776 (1993) and A. A. Y. Milne and P. P. Piper, "Role of VLA-4 integrin in leucocyte recruitment and bronchial hyperresponsiveness in the gunea-pig." *Eur. J. Pharmacol.*, 282, 243 (1995)); iii) adjuvant-induced arthritis in rats as a model of inflammatory arthritis (see C. Barbadillo et al., "Anti-VLA-4 mAb prevents adjuvant arthritis in Lewis rats." *Arthr. Rheuma.* (Suppl.), 36 95 (1993) and D. Seiffge, "Protective effects of monoclonal antibody to VLA-4 on leukocyte adhesion and course of disease in adjuvant arthritis in rats." *J. Rheumatol.*, 23, 12 (1996)); iv) adoptive autoimmune diabetes in the NOD mouse (see J. L. Baron et al., "The pathogenesis of adoptive murine autoimmune diabetes requires an interaction between $\alpha$4-integrins and vascular cell adhesion molecule-1.", *J. Clin. Invest.*, 93, 1700 (1994), A. Jakubowski et al., "Vascular cell adhesion molecule-Ig fusion protein selectively targets activated $\alpha$4-integrin receptors in vivo: Inhibition of autoimmune diabetes in an adoptive transfer model in nonobese diabetic mice." *J. inmunol.*, 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Tranplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts." *J. Clin Invest.*, 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L Chisholm et al., "Monoclonal antibodies to the integrin a-4 subunit inhibit the murine contact hypersensitivity response." *Eur. J. imunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "integrins and other adhesion molecules involved in melanocytic tumor progression.", *Curr. Opin. Oncol.*, 7, 185 (1995)); x) experimental autoimmune thyroiditis (see R. W. McMurray et al., "The role of $\alpha$4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996; xii) inhibition of TH2 T-cell cytokine production including IL-4 and IL-5 by VLA-4 antibodies which would attenuate allergic responses (J.Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas, including multiple myeloma; inflammatory lung disorders; acute respiratory distress syndrome (ARDS); pulmonary fibrosis; atherosclerotic plaque formation; restenosis; uveitis; and circulatory shock (for examples, see A. A. Postigo et al., "The $\alpha_4\beta_1$/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren®, Athena Neurosciences/Elan) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several antagonists of VLA-4 and $\alpha$4$\beta$7 have been described (D. Y. Jackson et al., "Potent $\alpha$4$\beta$1 peptide antagonists as potential anti-inflammatory agents", *J. Med. Chem.*, 40, 3359 (1997); H. N. Shroff et al., "Small peptide inhibitors of $\alpha$4$\beta$7 mediated MadCAM-1 adhesion to lymphocytes", *Bioorg. Med. Chem. Lett.*, 6, 2495 (1996); K C. Lin et al., "Selective, tight-binding inhibitors of integrin $\alpha$4$\beta$1 that inhibit allergic airway responses". *J. Med. Chem.*, 42, 920 (1999); U.S. Pat. No. 5,510,332, WO97103094, WO97/02289, WO96/40781, WO96122966, WO96/20216, WO96/01644, WO96/06108, WO95/15973). There are reports of nonpeptidyl inhibitors of the ligands for $\alpha_4$-integrins (WO99/36393, WO98/58902, WO96/31206); A. J. Soures et al., *Bioorg. Med. Chem. Lett.*, 8, 2297 (1998). There still remains a need for low molecular weight, specific inhibitors of VLA-4- and $\alpha$4$\beta$7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and $\alpha$4$\beta$7 binding and cell adhesion and activation.

DETAILED DESCRIPTION OF THE INVENTION

The present invention provides novel compounds of Formula I

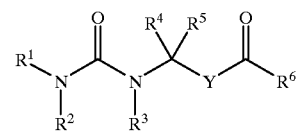

or a pharmaceutically acceptable salt thereof wherein:
  $R^1$ and $R^2$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^b$, provided that $R^1$ and R2 are not both hydrogen; or
  $R^1$ and $R^2$ together with the nitrogen to which they are attached form a mono- or bicyclic heterocycle each ring having 4 to 7 members and containing 0–2 additional heteroatoms independently selected from oxygen, sulfur and nitrogen, said heterocycle being optionally (1) fused to a benzene ring, or (2) spiro-fused to a 5- or 6-membered saturated or unsaturated ring optionally containing one heteroatom selected from O, S, and N and optionally fused to a benzene ring; wherein said heterocycle, benzene and spiro-fused ring are each optionally substituted with one to four groups selected from $R^b$;

$R^3$ is
1) hydrogen,
2) C1–10alkyl,
3) C2–10alkenyl,
4) C2–10alkynyl
5) cycloalkyl,
6) heterocyclyl,
7) aryl,
8) heteroaryl,
   wherein alkyl, alkenyl, alkynyl, cycloalkyl and heterocyclyl are optionally substituted with one to four substituents selected from $R^a$, and aryl and heteroaryl are optionally substituted with one to four substituents independently selected from $R^b$; or $R^2$ and $R^3$ together with the atoms to which they are attached form a heterocyclic ring of 5 to 7 members with the proviso that $R^1$ and $R^2$ do not form a ring;

$R^4$ is
1) $C_{1-10}$alkyl,
2) aryl,
3) aryl-$C_{1-10}$alkyl,
4) biaryl,
5) biaryl-$C_{1-10}$alkyl,
6) heteroaryl,
7) heteroaryl-$C_{1-10}$alkyl,
8) heteroaryl-aryl,
9) heteroaryl-aryl-$C_{1-10}$alkyl,
10) aryl-beteroaryl,
11) aryl-heteroaryl-$C_{1-10}$alkyl,
    wherein the alkyl group is optionally substituted with one to four substituents selected from $R^a$, and the aryl, biaryl, and heteroaryl groups are substituted with one to four substituents independently selected from $R^b$, $R^5$ is
1) hydrogen,
2) $C_{1-10}$alkyl,
3) $C_{2-10}$alkenyl,
4) $C_{2-10}$alkynyl,
   wherein alkyl, alkenyl and alkynyl are optionally substituted with one to four substituents independently selected from $R^a$;

$R^6$ is
1) OH,
2) $C_{1-10}$alkoxy,
3) $C_{2-10}$alkenoxy,
4) $C_{2-10}$alkynoxy,
5) ayloxy,
6) aryl-$C_{1-10}$alkoxy,
7) $NR^dR^e$,
   wherein alkyl, alkenyl and alkynyl are optionally substituted with one to four substituents selected from $R^a$, and aryl is optionally substituted with one to four substituents independently selected from $R^b$;

$R^7$ is
1) hydrogen,
2) $C_{1-10}$alkyl,
3) $C_{2-10}$alkenyl,
4) $C_{2-10}$alkynyl,
5) ayl,
6) aryl-$C_{1-10}$alkyl,
   wherein alkyl, alkenyl and alkynyl are optionally substituted with one to four substituents selected from $R^a$, and aryl is optionally substituted with one to four substituents independently selected from $R^a$;

$R^8$ is
1) hydrogen,
2) $C_{1-10}$alkyl,
3) $C_{2-10}$alkenyl,
4) $C_{2-10}$alkynyl,
5) aryl,
6) heteroaryl,
7) aryl $C_{1-10}$alkyl,
8) heteroaryl $C_{1-10}$alkyl,
9) —$OR^d$,
10) —$O(CR^fR^g)_nNR^dR^e$,
11) —$OC(O)R^d$,
12) —$OC(O)NR^dR^e$,
13) halogen,
14) —$SR^d$,
15) —$S(O)_mR^d$,
16) —$S(O)_2OR^d$,
17) —$S(O)_mNR^dR^e$,
18) —$NO_2$,
19) —$NR^dR^e$,
20) —$NR^dC(O)R^e$,
21) —$NR^dS(O)_mR^e$,
22) —$NR^dC(O)OR^e$, or
23) —$NR^dC(O)NR^dR^e$,
    wherein alkyl, alkenyl, alkynyl, aryl, heteroaryl are optionally substituted with one to four substituents selected from a group independently selected from $R^c$;

$R^a$ is
1) hydrogen,
2) —$OR^d$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N$—$OR^e)$,
22) $CF_3$; or
23) —$OCF_3$;

$R^b$ is
1) a group selected from $R^a$,
2) $C_{1-10}$alkyl,
3) $C_{2-10}$alkenyl, 4) $C_{2-10}$alkynyl,
5) Cy;
6) Cy–$C_{1-10}$alkyl,
   wherein alkyl, alkenyl, alkynyl, and Cy are optionally substituted with one to four substituents selected from a group independently selected from $R^c$;

$R^c$ is
1) halogen,
2) NRfRg,
3) carboxy,
4) $C_{1-4}$alkyl optionally substituted with C(O)O-C1–4alkoxy,
5) $C_{1-4}$alkoxy,
6) aryl,
7) aryl $C_{1-4}$alkyl,
8) hydroxy,
9) $CF_3$, or
8) aryloxy; or
   two $R^c$ groups on adjacent atoms of a benzene ring together form methylenedioxy; $R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0–2 additional heteroatoms independently selected from oxygen, sulfur and nitrogen;

$R^f$ and $R^g$ are independently selected from hydrogen, $C_{1-10}$alkyl, Cy and Cy–$C_{1-10}$alkyl; or $R^f$ and $R^g$ together with the carbon to which they are attached form a ring of 5 to 7 members containing 0–2 heteroatoms independently selected from oxygen, sulfur and nitrogen;

Cy is independently selected from cycloalkyl, heterocyclyl, aryl, or heteroaryl;

m is an integer from 1 to 2;
n is an integer from 1 to 10;
Y is
1) a bond, or
2) —C($R^7$)($R^8$)—

In one embodiment of compounds of formula I, R1 is hydrogen or C1–5alkyl, and R2 is selected from Cy and Cy-C1–5=l alkly wherein Cy is optionally substituted with one to four substituents independently selected from $R^b$.

In another embodiment of compounds of formula I, $R^1$ and $R^2$ together with the nitrogen to which they are attached form a mono- or bicyclic heterocycle each ring having 4 to 7 members and containing 0–2 additional heteroatoms independently selected from oxygen, sulfur and nitrogen, said heterocycle being optionally (1) fused to a benzene ring, or (2) spiro-fused to a 5- or 6-membered saturated or unsaturated ring optionally containing one heteroatom selected from O, S, and N and optionally fused to a benzene zing; wherein said heterocycle, benzene and spiro-fused ring are each optionally substituted with one to four groups selected from $R^b$. Examples of ring systems (which may be optionally substituted as described above) include pyrrolidine, morpholine, piperidine, thiamorpholine, azacycloheptane, tetrahydroquinoline, tetaydroisoquinoline, 2-azabicyclo[3.2.1]octane, 3,4-benzo-2,8-diazaspiro[4.5]decane, 3,4-benzo-8-azaspiro[4.5]decane, 3,4-benzo-8-azaspiro[4.5]dec-1-ene. In a preferred embodiment $R^1$ and $R^2$ together with the nitrogen to which they are attached form a mono- cyclic heterocycle having 4 to 7 members and containing 0–2 additional heteroatoms independently selected from oxygen, sulfur and nitrogen, said heterocycle being optionally substituted with one to four groups selected from phenyl optionally substituted with halogen or $C_{1-3}$alkoxy, benzyl, $C_{1-5}$alkyl optionally substituted with hydroxy or NR$^f$Rg, $CO_2R^d$, C(O)$R^d$, and C(O)NR$^d$R$^e$.

In another embodiment, $R^3$ is hydrogen.

In another embodiment $R^5$ is hydrogen, and $R^4$ is biaryl-$C_{1-5}$alkyl wherein aryl is optionally substituted with one to four groups selected from $R^b$. Preferably $R^4$ is biphenyl-methyl optionally substituted with one or two groups selected from $R^b$. More preferably $R^4$ is biphenylmethyl substituted with one or two groups selected from $R^b$, and wherein one of the substituents is attached to the 2'-position. Even more preferred, $R^4$ is selected from 2'-cyano-biphenylmethyl, 2'-methoxy-biphenylmethyl and 2',6'-bis(methoxy)biphenylmethyl.

In another embodiment Y is a bond.

In another embodiment $R^6$ is OH or a pharmaceutically acceptable salt thereof.

Examples of compounds of the present invention include:

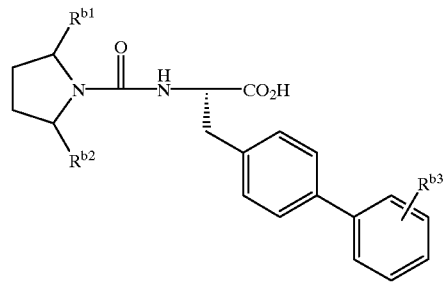

| $R^{b1}$ | $R^{b2}$ | $R^{b3}$ |
|---|---|---|
| H | PhCH$_2$OC(O) | H |
| H | CH$_3$OC(O) | H |
| CH$_3$ | CH$_3$ | H |
| H | H | H |
| H | PhNHCH$_2$ | H |
| H | OHCH$_2$ | H |
| H | H | 2-CN |
| H | CH$_3$OC(O) | 2-CH$_3$O |
| H | OHCH$_2$ | 2,6-diCH$_3$O |

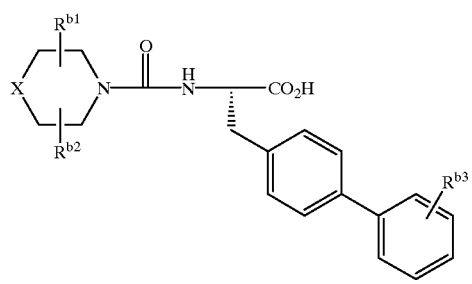

| X | $R^{b1}$/$R^{b2}$ | $R^{b3}$ |
|---|---|---|
| CH$_2$ | 3-PhCH$_2$/3-(CH$_3$CH$_2$OC(O)) | 2-CN |
| PhC(O)CH | H/H | 2-CN |

-continued

| | | |
|---|---|---|
| [indoline-N-SO2CH3 structure] | H/H | 2-CN |
| (CN)(Ph)C | H/H | 2-CN |
| 2-(CH3CH2OC(O)CH2CH2)—Ph—CN | H/H | 2-CN |
| (2-CH3OPh)—N | H/H | CN |
| CH2 | H/3-PhCH2 | 2-CN |
| [indane-C(O)N(CH3)2 structure] | H/H | 2-CN |
| (Ph2CH)N | H/H | 2-CN |
| [benzodioxole-CH2-N structure] | H/H | 2-CN |
| [indene structure] | H/H | 2-CN |
| 2-ClPhC(O)CH | H/H | 2-CN |
| (Ph)(NH2C(O))C | H/H | 2-CN |
| PhCH2CH | H/H | 2-CN |
| [indane-C(O)OCH2CH3 structure] | H/H | 2-CN |
| O | H/H | 2-CN |
| CH3CH2OC(O)CH | H/H | 2-CN |
| PhCH2N | H/H | 2-CN |
| (2-ClPh)N | H/H | 2-CN |
| CH2 | H/H | 2-CN |
| [indoline-N-SO2CH3 structure] | H/H | 2-CH3O |
| PhC(O)CH | H/H | 2-CH3O |
| O | H/H | 2-CH3O |
| [benzodioxole-CH2-N structure] | H/H | 2-CH3O |
| [2-furanyl-C(O)-N structure] | H/H | 2-CH3O |
| [indane-C(O)OCH2CH3 structure] | H/H | 2-CH3O |
| [indane structure] | H/H | 2-CH3O |
| O | H/H | 2,6-diCH3O |
| CH2 | H/H | 2,6-diCH3O |
| CH3CH | H/H | 2,6-diCH3O |
| CH3CH | H/3-CH3 | 2,6-diCH3O |
| CH2 | 3-CH3/5-CH3 | 2,6-diCH3O |
| CH2CH2 | H/H | 2,6-diCH3O |
| PhCH2CH | H/H | 2,6-diCH3O |
| CH3CH2OC(O)CH | H/H | 2,6-diCH3O |
| CH2 | H/2-CH3 | 2,6-diCH3O |
| CH2 | 3-(CH3CH2OC(O)) | 2,6-diCH3O |
| (1-piperidinyl)CH | H/3-CH3 | 2,6-diCH3O |
| CH2 | 2-CH3/6-CH3 | 2,6-diCH3O |
| CH3N | H/H | 2,6-diCH3O |
| CH2 | H/3-PhCH2 | 2,6-diCH3O |
| PhN | H/H | 2,6-diCH3O |
| S | H/H | 2,6-diCH3O |

[structure: R2-N(H)-C(O)-N(R1)- attached to CH(CO2H)-CH2- connected to biphenyl with Rb substituent]

| R1 | R2 | Rb |
|---|---|---|
| 2-tetrahydrofurylmethyl | H | H |
| Ph | H | 2-CN |
| Ph | CH3 | 2-CN |
| CH3 | CH3 | 2-CN |
| CH3 | CH3 | 2-CH3O |
| 3-(CH3O)Ph | H | 2,6-diCH3O |

-continued

| | | |
|---|---|---|
| 3-(CH₃)Ph | H | 2,6-diCH₃O |
| 4-F-Ph | H | 2,6-diCH₃O |
| Ph | H | 2,6-diCH₃O |
| benzyl | H | 2,6-diCH₃O |
| cHex | H | 2,6-diCH₃O |
| 1-napthylethyl | H | 2,6-diCH₃O |
| 2-CH₃OC(O)Ph | H | 2,6-diCH₃O |
| 3,5-diCF₃-Ph | H | 2,6-diCH₃O |
| 3,5-diCl-Ph | H | 2,6-diCH₃O |
| 4-(CH₃CH₂OC(O))Ph | H | 2,6-diCH₃O |
| 2-CH₃O-Ph | H | 2,6-diCH₃O |
| 2-CH₃-Ph | H | 2,6-diCH₃O |
| 2,5-diCl-Ph | H | 2,6-diCH₃O |
| n-C₆H₁₃ | CH₃ | 2,6-diCH₃O |
| Ph | CH₃ | 2,6-diCH₃O |

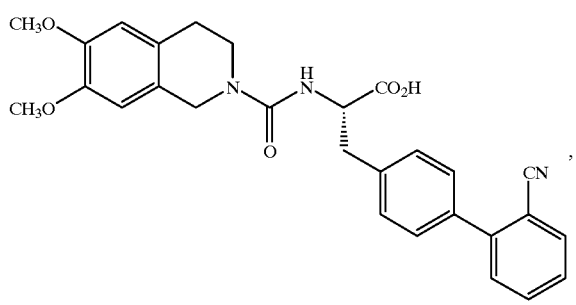

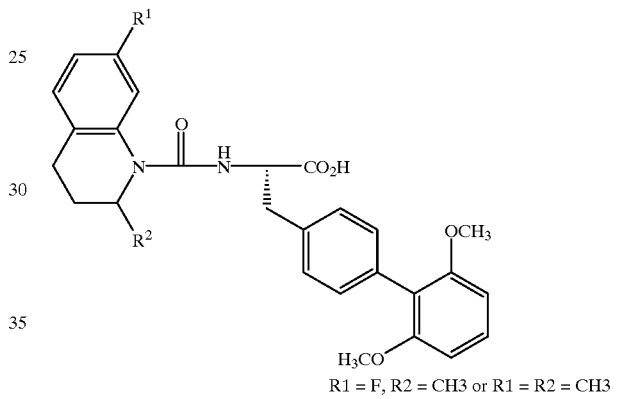

R1 = F, R2 = CH3 or R1 = R2 = CH3

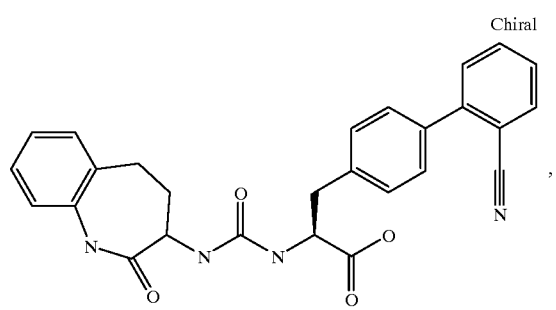

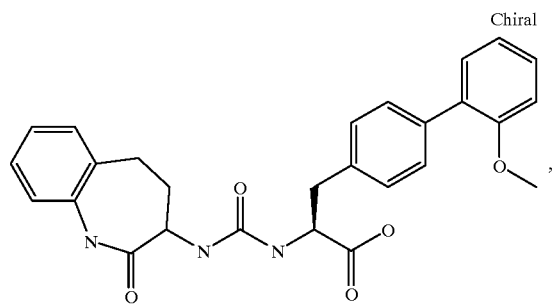

The present invention provides, in another aspect, a method for the prevention or treatment of diseases, disorders, conditions or symptoms mediated by cell adhesion in a mammal which comprises administering to said mamal an effective amount of a compound of Formula I. More particularly said disease or disorder is selected from asthma, allergic rhinitis, multiple sclerosis, atherosclerosis, and inflammatory bowel disease.

In another aspect the present invention provides a method for preventing the action of VLA-4 in a mammal which comprises administering to said mammal a thereapeutically effective amount of a compound of formula I.

Another aspect of the present invention provides a pharmaceutical composition which comprises a compound of formula I and a pharmaceutically acceptable carrier.

Unless otherwise specified the following terms have the given meanings:

"Akyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, morpholine, thiamorpholine, benzoazacycloheptyl, azacycloheptyl, azabicyclo[3.2.1]octyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)pyximidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as ketonol tautomers. The individual tautomers as well as mixture thereof are encompassed with compounds of Formula I.

Compounds of the Formula I may be separated into diastereoisomeric pairs of enantiomers by, for example, factional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic gases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Fomula I to antagonize the actions of VLA-4 and/or $\alpha 4\beta 7$ integrin makes them useful for preventing or reversing the symptoms, disorders or diseases induced by the binding of VLA-4 and or $\alpha 4\beta 7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha 4\beta 7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) hepatitis and (20) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukatst, iralukast, pobilukast, SKB-106,203), leukotriene biosynthesis inhibitors (zileuton, BAY-1005); (f) non-steroidal antiinflammatory agents (NSAIDs) such as propionic acid derivatives (alrinoprofen, benoxaprofen, bucloxic acid, carprofen, fenbufen, fenoprofen, fluprofen, flurbiprofen, ibuprofen, indoprofen, ketprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In the first method (Scheme 1), a resin-based synthetic strategy is outlined where the resin employed is represented by the ball (◉). An N-Fmoc-protected amino acid derivative A (Fmoc=fluorenylmethoxycarbonyl) is loaded on to the appropriate hydroxyl-containing resin (the choice of resin being dependent on type of linker used, in this case Wang resin was utilized) using 1-ethyl-3-(3'-dimethylaminopropyl)carbodiimide (EDC) and 4-dimethylaminopyridine (4-DMAP) in a solvent such as methylene chloride and teterahydrofuran or dimethylformamide (DMF) to give B. The Fmoc protecting group is removed with piperidine in DMF to yield free amine C. A reactive carbonyl reagent such as 4-nitrophenylchoroformate in the presence of a base such as diisopropylethylaniine is added to a slurry of C and, following washing, is reacted with an amine D to form urea E. Alternatively, C may be reacted with an isocyante reagent F to form E directly. The final product is removed from the resin with strong acid (in this instance, trifluoroacetic acid to yield compounds of the present invention G.

reagent such as 4-nitrophenylchoroformate in the presence of a base such as diisopropylethylamine is added to a solution of A which is subsequently reacted with an amine B to form urea D. Alternatively, A may be reacted with an isocyante reagent C to form D directly. The final product is hydrolyzed with strong acid (in this instance, trifluoroacetic acid) if D is a tert-butyl ester or hydroxide if D is a methyl ester to yield compounds of the present invention E.

Scheme 2

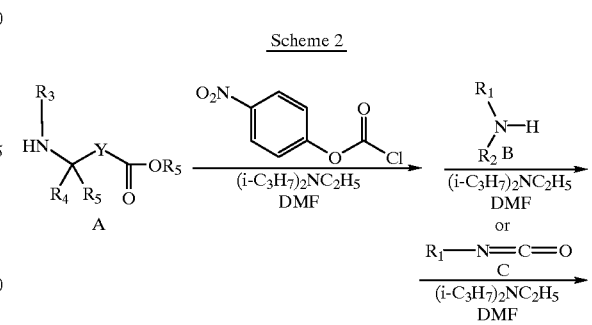

Scheme 1

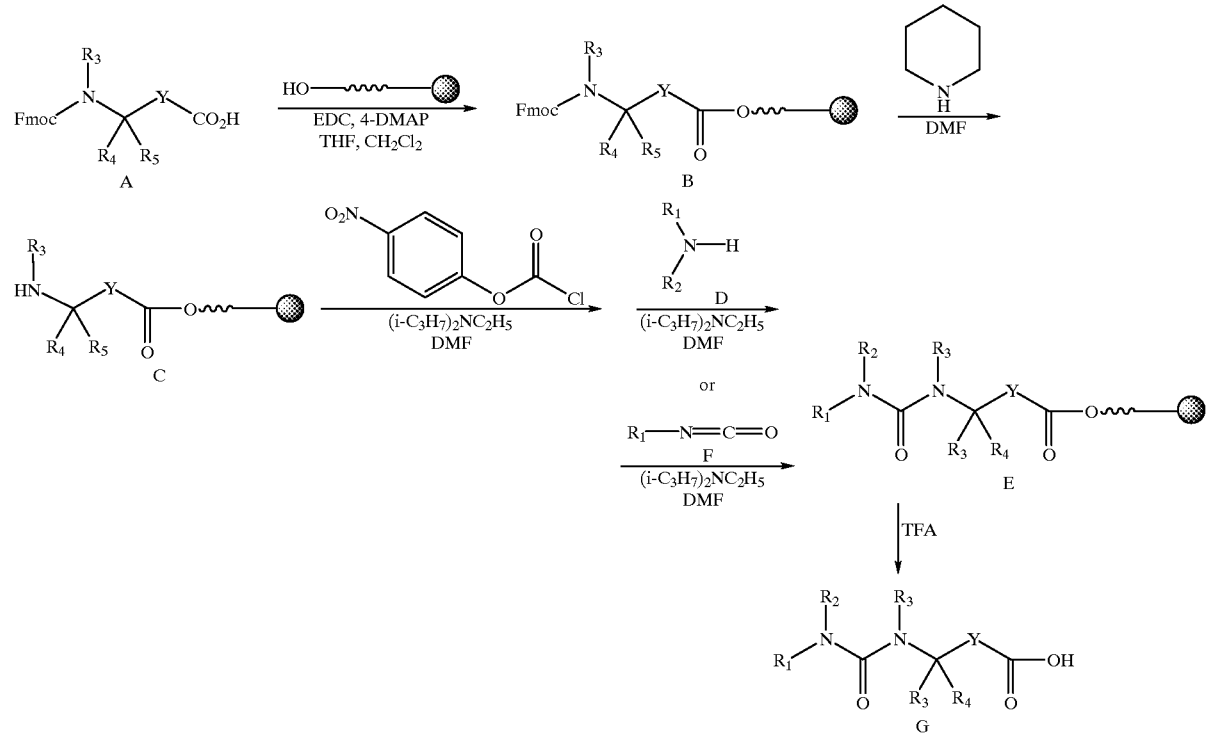

In the second method (Scheme 2), standard solution phase synthetic methodology is outlined. Many amino acid derivatives are commercially available as the t-butyl or methyl esters and may be used directly in the synthesis outlined below. Amino acid t-butyl esters A may be prepared from amino acids directly by treament with isobutylene and sulfuric acid in diglyme or dioxane. Alternatively, N-Boc-protected amino acid derivative is treated with tert-butyl 2,2,2-trichloroacetimidate in the presence of boron trifluoride etherate followed by treatment with strong acid (HCl in ethyl acetate or sulfuric acid in t-butyl acetate) to remove the t-BOC group to yield tert-butyl ester A. A reactive carbonyl -continued

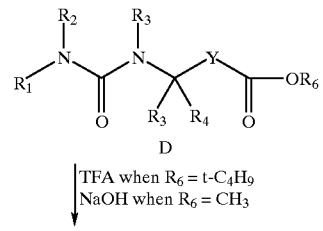

-continued

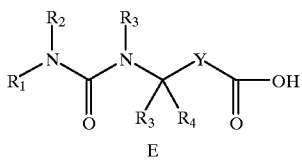

E

In a third method (Scheme 3), a late stage intermediate aryl bromide or iodide is coupled to an appropriately substituted aryl or heteroaryl boronic acid to give a subset of compounds of the present invention ($R^4$=biaryl-substituted-alkyl or heteroaryl-aryl-substituted-alkyl, $R^3$=hydrogen). For example, 4-iodo or 4-bromophenyl-derivative A is converted to the t-butyl ester B by treatment with isobutylene and sulfuric acid. Alternatively the N-Boc-4-iodo- or 4-bromo-phenyl-derivative C is reacted with tert-butyl 2,2, 2-trichloroacetimidate in the presence of boron trifluoride etherate in methylene chloride-cyclohexane followed by treatment with strong acid Scheme 3

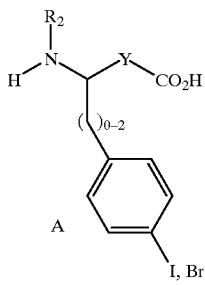

A

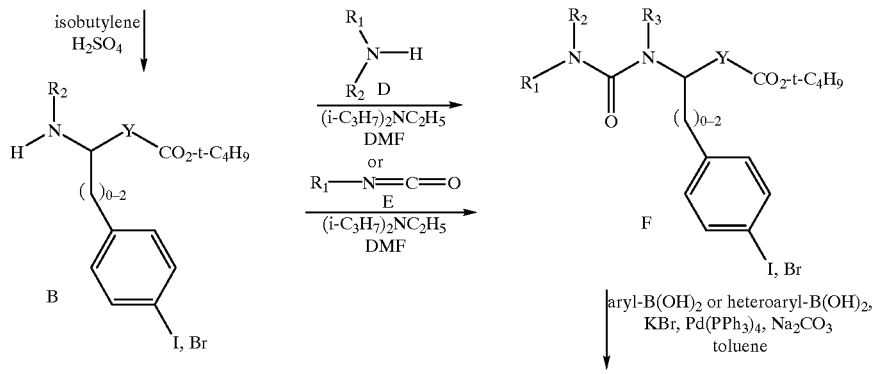

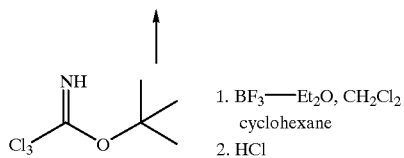

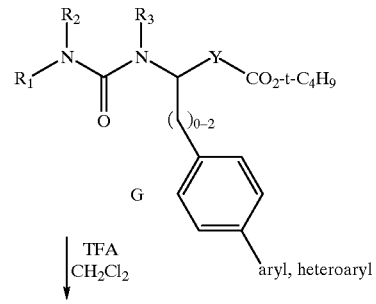

-continued

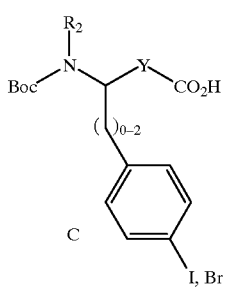

C

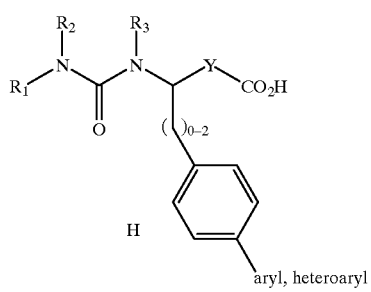

H (HCl in ethyl acetate or sulfuric acid in t-butyl acetate) to remove the t-BOC group to yield tert-butyl ester B which is subsequently reacted with p-nitrophenylchloroformate and amine D or directly with isocyanate E as described above to yield urea F. Substituted aryl or heteroaryl boronic acids are coupled to F in the presence of a palladium(0) reagent, such as tetrakis(triphenylphosphine)palladium under Suzuki conditions (N. Miyaura et al., *Synth. Commun.*, 1981, 11, 513–519) to yield G. The tert-butyl ester is then removed by treatment with strong acid (TFA) to yield the desired product H. If the aryl or heteroaryl boronic acid is not commercially available, but the corresponding bromide or iodide is, then the bromide or iodide can be converted into the desired boronic acid by treatment with an alkyllithium reagent in tetrahydrofuran at low temperature followed by addition of trimethyl or triisopropyl borate. Hydrolysis to the boronic acid can be effected by treatment of the intermediate with aqueous base and then acid.

Alternatively, the aryl coupling reaction may be performed by application of Stille-type carbon-carbon bond forming conditions (Scheme 4). (A. M. Echavarren and J. K. Stille, *J. Am. Chem. Soc.* 1987, 109, 5478–5486). The aryl bromide or iodide intermediate A (described in Scheme 3) is converted into its trialkyltin derivative B using hexamethylditin in the presence of a palladium(0) catalyst and lithium chloride and then reacted with an appropriately substituted aryl or heteroaryl bromide, iodide, or triflate in the presence of a palladium reagent, such as tetrakis(triphenylphosphine) palladium(0) or tris(dibenzylideneacetone)dipalladium(0), in a suitable solvent, such as toluene, dioxane, DMF, or 1-methyl-2-pyrrolidinone, to give intermediate C. The tert-butyl ester is then removed by treatment with strong acid (TFA) to yield the desired product D. Biphenyl amino acids suitable for attachment to resin (D where $R_1$ is fluorenylmethyloxy) may be prepared by this route as well. Superior coupling conversions and rates may be elicited by application of the method of Farina (*J. Org. Chem.* 5434, 1993)

Scheme 4

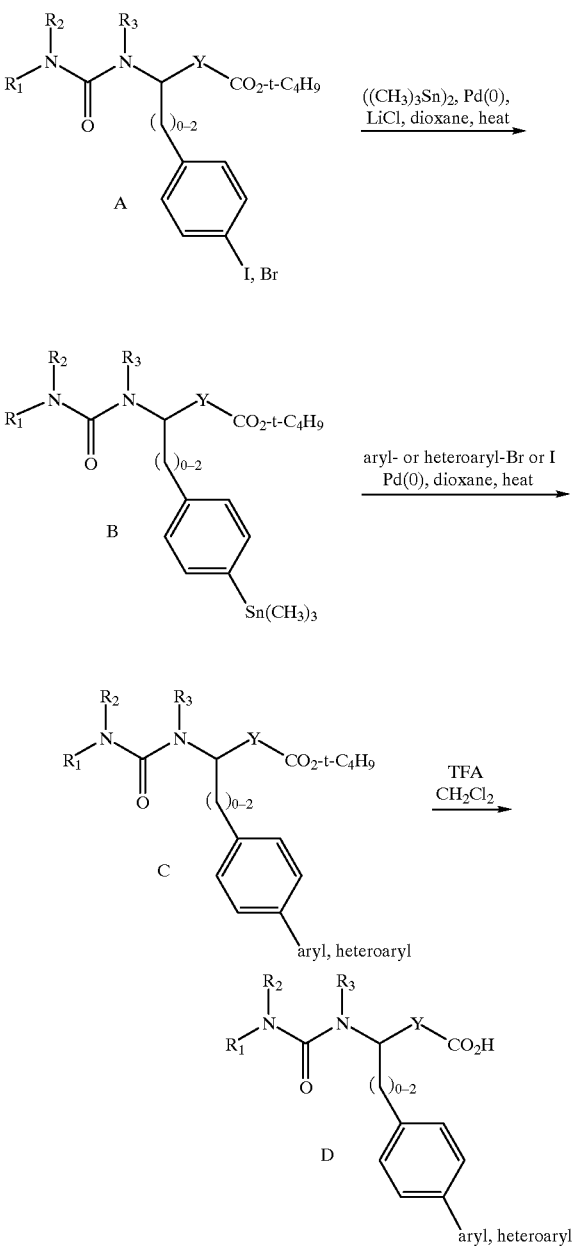

Compounds wherein the middle ring is heteroaryl (E) may be prepared (Scheme 5) in a similar fashion starting from the appropriate heteroaryl bromide or iodide D using Suzuki-type conditions as depicted in Scheme 3 or from the corresponding heteroaryl trimethyltin using Stille-type conditions as depicted in Scheme 4. The requisite heteroaryl halides D may be prepared via conventional electrophilic halogenation of the N-Boc-heteroaryl-alanine tert-butyl ester interrmediate B. B may be prepared from the known aliphatic iodo intermediate A in carbon-carbon bond formation using zinc/copper couple and palladium(II) (M. J. Dunn et al., SYNLETT 1993, 499–500).

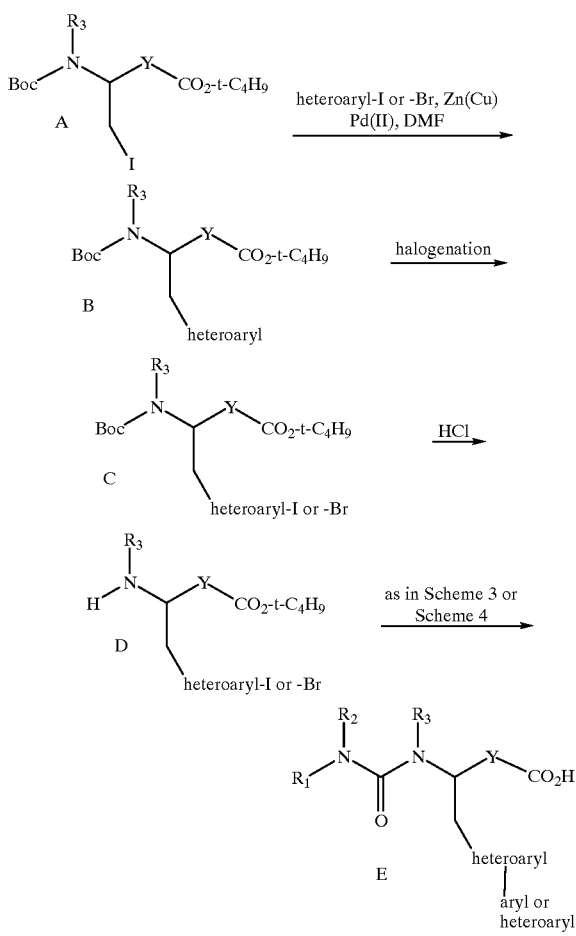

Reference Example 1
N-FMOC-(L)-4-(2'-cyanophenyl)phenylalanine
Step A
N-FMOC-(L)-4-iodophenylalanine, t-butyl Ester To a solution of 15 g (51 mmol) of (L)-4-iodophenylalanine in 100 ml of diglyme and 15 ml of concentrated $H_2SO_4$ was added 30 ml of condensed isobutylene. The vessel was agitated overnight and the crude product was diluted with 100 ml of ethyl acetate. The solution was added to excess sodium hydroxide solution while maintaining the temperature below 30° C. A white precipitate formed which dissolved upon addition of sodium hydroxide solution. The resulting mixture was filtered and the aqueous phase was extracted with ethyl acetate. The combined extracts were washed with brine and dried over anhydrous magnesium sulfate. The mixture was filtered and concentrated in vacuo to give a solution of the product in diglyme. The solution was diluted with 200 ml of ether and was treated with excess 1N HCl in ether with rapid stirring. The resulting precipitate was collected and dried in vacuo after washing with ether. A white solid (9.01 g) was collected of 4-iodophenylalanine t-butyl ester hydrochloride. To a suspension of 5.1 g (13.3 mmol) of the amnine hydrochloride in 30 ml of methylene chloride was added 3.6 g (27 mmol) of diisopropyl ethyl amine followed by 3.43 g (0.013 g) of FMOCCl. The solution was stirred overnight at room temperature, washed with 1N HCl solution (3×50 ml), water (1×50 ml), saturated sodium carbonate solution (2×50 ml) and brine (1×50 ml). The solution was dried over $MgSO_4$, filtered and concentrated in vacuo to give 6.43 g of N-FMOC-(L)-4-iodophenylalanine, t-butyl ester as a white foam.

300 MHz $^1H$ NMR ($CDCl_3$): d 1.44 (s, 9H); 3.05 (d, 2H);4.20–4.60 (m, 4H); 5.30 (m, 1H); 6.90 (d, 2H), 7.30–7.80 (m, 12H).

Step B
N-FMOC-(L)-4-trimethylstannyl-phenylalanine, tert-butyl Ester

In a dry 250 ml round bottom flask was added 6.20 g (10.5 mmol) of the product of Step A, 0.48 g (115 mmol) LiCl and 0.6 g (0.52 mmol) of palladium tetrakistriphenylphosphine followed by 50 ml of dry dioxane. The mixture was stirred for 5 minutes. 5.2 g (15.8 mmol) of hexamethylditin was added and the reaction mixture was degassed and then heated at 90° C. The reaction mixture gave a black suspension after 15 minutes. Completion of the conversion was determined by TLC (10% EtOAc/hexanes; sm r.f.=0.3, product r.f.=0.4). The mixture was diluted with 100 ml of hexanes and stirred to give a precipitate. The suspension was filtered through celite and concentrated in vacuo to give a gum. The residue was purified by flash chromatography over silica gel eluting with 10% EtOAc/hexanes to give 5.02 g of the stannane (77% yield).

300 MHz $^1H$ NMR ($CDCl_3$): d 0.30 (s, 9H); 1.45 (s, 9H); 3.20 (d, 2H), 4.20–4.60 (m, 4H); 5.29 (d, 1H); 7.12 (d, 2H); 7.22–7.45 (m, 6H); 7.59 (d, 2H), 7.75 (d, 2H).

Step C
N-FMOC-(L)-4-(2'-cyanophenyl)phenylalanine, tert-butyl Ester

In a clean, dry round bottom flask fitted with a reflux condenser vented through a three way valve attached to a vacuum source and nitrogen gas was added 1.56 g (6.8 mmol) of 2-iodobenzonitrile, 0.117 (0.12 mmol) of tris (dibenzylidineacetone)-dipalladium (0), 0.8 g (19 mmol) of LiCl and 0.15 g (0.5 mmol) of triphenylarsine followed by 30 ml of N-methylpyrrolidinone (NMP). The mixture was degassed and stirred for 10 minutes at which time most of the catalyst mixture had dissolved. 3.9 g (6.21 mmol) of the product of Step B was added in 10 ml of NMP and the reaction was heated to 80° C. for 90 minutes. TLC (10% EtOAc/hexanes) indicated complete consumption of stannane (rf=0.4) and formation of the desired product (rf=0.1). The solution was cooled to room temperature and diluted with 50 ml of EtOAc. The solution was stirred with 20 ml of saturated KF for 20 minutes. The mixture was diluted with 200 ml of EtOAc and washed with water (6×75 ml), brine (1×50 ml) and was dried over $MgSO_4$. The mixture was filtered and concentrated in vacuo and the residue was purified by Biotage Flash chromatography over silica gel eluting with 20% EtOAc/hexanes to give 1.91 g (54% yield) of the title compound.

300 MHz $^1H$ NMR ($CDCl_3$): d 1.45 (s, 9H); 3.19 (d, 2H); 4.20–4.68 (m, 4H); 5.40 (d, 1H); 7.25–7.55 (m, 12H); 7.65 (m, 2H), 7.80 (d, 2H).

Step D
N-FMOC-(L)-4-(2'-cyanophenylphenylalanine 2.4 g of the product of Step C was treated with 50 ml of a mixture of 50% trifluoroacetic acid in methylene chloride. The reaction mixture was concentrated in vacuo. The residue was azeotropically dried by concentration from toluene to give the desired product as a foam.

300 MHz $^1$H NMR (CD$_3$OD): d 3.02 (dd, 1H); 3.30 (dd, 1H); 4.05–4.35 (m, 3H); 4.52 (m, 1H); 7.10–7.50 (m, 12H); 7.60 (m, 2H), 7.78 (d, 2H).

Reference Example 2
N-(FMOC)-(L)-4-(2'-methoxyphenyl)phenylalanine
Step A
N-(Boc)-(L)-4-iodphenylalanine, tert-butyl Ester To a suspension of 7.5 g (0.019 m) of 4-iodophenylalanine t-butyl ester (Reference Example 1 Step A prior to treatment with HCl) in 100 ml of dichloromethane was added 2.52 g 0.019 m of diisopropyl ethyl amine followed by 4.14 g of ditertbutyldicarbonate. The reaction mixture was stirred over night at room temperature, washed with 1N HCl (2×25 ml), water (2×25 ml), saturated NaHCO$_3$ (1×25 ml), brine (1×25 ml) and was dried over MgSO$_4$. The mixture was filtered and concentrated in vacuo to to give the desired product as a gum 8.8 g (100% yield).

300 MHz $^1$H NMR (CDCl$_3$): δ1.39 (s, 18H); 2.98 (AB, 2H); 4.4 (dd, 2H); 5.0 bd, 1H); 6.92 (d, 2H); 7.62 (d, 2H).
Step B
N-(Boc)-(L)-4-(2'-methoxyphenyl)phenylalanine, tert-butyl Ester 7.97 g (0.018 m) of the product of Step A was dissolved in 160 ml of 2:1 toluene:ethanol. To this solution was added 2.99 g (0.0198 m) 2-methoxyphenylboronic acid, 0.69 g of tetrakistriphenylphosphine palladium (0) and 22.7 ml (0.45 m) of 2.0 M sodium carbonate in water. The reaction mixture was degassed three times and then heated at 90° C. for 90 minutes at which time the reaction mixture was black. The mixture was diluted with 300 ml of ethyl acetate and was washed with water (3×150 ml) and brine (2×100 ml) and was dried over MgSO$_4$. The mixture was filtered and concentrated in vacuo. The residue was purified by flash chromatography over silica gel eluting with 10% EtOAc/hexanes to give 6.89 g (88% yield) of the desired product as a white solid.

300 MHz $^1$H NMR (CDCl$_3$): δ1.45 (s, 18H); 3.10 (d, 2H); 3.80 (s, 3H); 4.5 (dd, 2H); 5.1 bd, 1H); 7.0 (m, 2H); 7.22 (d, 2H); 7.30 (d, 2H); 7.49 (d, 2H); 7.62 (d, 2H).
Step C
N-(FMOC)-(L)-4-(2'-methoxyphenyl)phenylalanine To a solution of 4.85 g (0.0113 m) of the product of Step B in 100 ml of t-butyl acetate was added 5.53 g (0.056 m) of concentrated sulfuric acid. The solution was stirred at room temperature for 2 hours and then carefully neutralized by addition of saturated aqueous NaHCO$_3$ solution. The solution was washed with NaHCO$_3$ solution, dried over NaSO$_4$, filtered and concentrated in vacuo. To a solution of 4.42 g of amine in 150 ml of methylene chloride was added at 0° C. 1.74 g (13.5 mmol) of diisopropylethyl amine followed by 3.48 g (13.5 mmol) of FMOCCl. The solution was stirred for 2 hours and washed with 1N HCl (3×50 ml), saturated NaHCO$_3$ solution (2×50 ml) and brine (1×50 ml). The mixture was filtered and concentrated in vacuo. The residue was purified by flash chromatography over silica gel eluting with a gradient of 10–25% EtOAc/hexanes to give 7.10 g (88% yield) of the desired product as a glass. The material was dissolved in 125 ml of 50% trifluoroacetic acid/methylene chloride and stirred at room temperature for 2.5 hours. The solution was concentrated in vacuo and the residue was redissolved in toluene and concentrated in vacuo to give 7.01 g of the desired product. 96% pure by HPLC (254 nm).

300 MHz $^1$H NMR (CDCl$_3$): δ3.20 (m, 2H); 3.76 (s, 3H); 4.21 (t, 1H); 4.41 (m, 4H); 4.76 (dd, 1H); 5.32 (d, 1H); 6.8–7.8 (m, 16H).

Reference Example 3
N-(FMOC)-(L)-4-(1-pyrrolidino-carbonyloxy)phenylalanine
Step A
N-(Boc)-(L)-tyrosine, tert-butyl Ester To a solution of 9.82 g (0.041 m) of (L)-tyrosine, tert-butyl ester in 150 ml of methylene chloride and 20 ml of DMF was added 5.2 g (0.04 m) of triethyl amine followed by 9.03 g (0.04 m) of ditertbutyldicarbonate. The reaction mixture was stirred for 2 hours at room temperature and was then washed with 1 N HCl (3×50 ml), NaHCO$_3$ solution (1×50 ml) and brine (1×50 ml) and was dried over MgSO$_4$. The mixture was filtered and concentrated in vacuo to give 13.59 g (98% yield) of a white solid.

300 MHz $^1$H NMR (CDCl$_3$): 1.42 (s, 18H); 2.95 (d, 2H); 4.39 (dd, 1H); 5.01 (d, 1H); 6.15 (s, 1H); 6.70 (d, 2H); 7.00 d, 2H).
Step B
N-(Boc)-(L)-4-(1-pyrrolidino-carbonyloxy)phenylalanine, tert-butyl Ester To a solution of 8.18 g (0.024 m) of the product of Step A in a clean, dry flask dissolved in 100 ml of THF under a dry nitrogen atmosphere was added at 0° C. 25.5 ml (0.025 m) of a 1M solution of sodium hexamethyldisilazide in THF. The solution was stirred for 20 minutes. A solution of 3.2 g (0.024 m) of pyrrolidine carbamoyl chloride in 10 ml of THF was added. The reaction mixture was allowed to warm to room temperature and was stirred for 48 hours. The solution was diluted with 100 ml of ethyl acetate and was washed with 1N HCl (3×75 ml), saturated NaHCO$_3$ (1×75 ml), 1N NaOH (2×75 ml) and brine (1×75 ml) and was dried over MgSO$_4$. The mixture was filtered and concentrated in vacuo and the residue was recrystalized from ethyl acetate/hexanes to give 8.6 g of a white solid.

300 MHz $^1$H NMR (CDCl$_3$): δ1.40 (s, 9H); 1.41 (s, 9H); 1.92 (m, 4H); 3.02 (d, 2H); 3.45 (t, 2H); 3.55 (t, 2H); 4.42 (dd, 1H); 4.99 (d, 1H); 7.05 (d, 2H); 7.15 (d, 2H).
Step C
N-FMOC)-(L)-4-(1-pyrrolidino-carbonyloxy)phenylalanine The method of Reference Example 2 Step C was applied to 8.1 g (0.018 m) of the product of Step A to give 6.27 g of the title compound as a foam. 71% overall yield.

300 MHz $^1$H NMR (CDCl$_3$): δ1.97 (bs, 4H); 3.12 (bd, 2H); 3.4–3.6 (2 bm, 4H); 4.20 (m, 1H); 4.30–4.50 (m, 2H); 4.69 m, 1H); 5.59 (t, 1H); 7.00–7.42 (m, 8H); 7.55 (bm, 2H); 7.77 (d, 2H).

Reference Example 4
(L)-4-(2'-methoxyphenyl)phenylalanine, tert-butyl Ester Hydrochloride To a solution of 4.85 g (0.0113 m) of the product of Reference Example 2 Step B in 100 ml of t-butyl acetate was added 5.53 g (0.056 m) of concentrated sulfuric acid. The solution was stirred at room temperature for 2 hours and then carefully neutralized by addition of saturated aqueous NaHCO$_3$ solution. The solution was washed with NaHCO$_3$ solution, dried over NaSO$_4$, filtered and concentrated in vacuo. The residue was dissolved in 50 ml of ether and treated with anhydrous HCl gas with stirring to give a white precipitate. The solid was collected by filtration, washed with ether and dried in vacuo to give the desired product. 300 MHz $^1$H NMR (CD$_3$OD): 1.45 (s, 9H); 3.20 (d, 2H); 3.79 (s, 3H); 4.21 (t, 1H); 7.03 (m, 2H); 7.28 (m, 2H); 7.31 (d, 2H); 7.50 (d, 2H).

Reference Example 5
(L)-4-(2',6'-Dimethoxyphenyl)phenylalanine, t-butyl Ester

To a solution of 18.5 g (55 mmol) of N-(Boc)-L-tyrosine, t-butyl ester (Reference Example 3, Step A) in 150 ml of dry methylene chloride was added 17.4 g (220 mmol) of pyridine followed at 0° C. by the addition of 18.6 g (66 mmol) of triflic anhydride neat dropwise. The reaction mixture was stirred at 0° C. and monitored by TLC. After 4 hours the mixture was diluted with 200 ml of methylene chloride and was washed with 1N HCl (3×100 ml), saturated sodium bicarbonate (2×100 ml) and brine (1×50 ml). The solution was dried over MgSO$_4$, filtered and concentrated in vacuo to give an oil. The oil was dissolved in a mixture of 125 ml of toluene and 61 ml of ethanol. To this solution was added 11.3 g (62 mmol) of 2,6-dimethoxyboronic acid and 2.5 g of palladium tetrakistriphenylphosphine. The solution was treated with 18.3 g (133 mmol) of potassium carbonate dissolved in 30 ml of water. The mixture was heated to reflux over 4 hours, diluted with 200 ml of ethyl acetate and was washed with water (3×75 ml), brine (1×75 ml) and was dried over MgSO$_4$. The mixture was filtered and concentrated in vacuo and the residue was purified by flash chromatography over silica gel eluted with a gradient of 5–20% EtOAc/hexanes to provide 14.7 g of N-(Boc)-(L)-4-(2',6'-dimethoxyphenyl)phenylalanine, t-butyl ester as a white solid. The solid was dissolved in 350 ml of t-butyl acetate at 0° C. and was treated with 8.3 ml of concentrated sulfuric acid. The cold bath was removed and after one hour TLC indicated only starting material was present. The reaction mixture was cooled in an ice bath once more and treated with 3.4 ml of concentrated sulfuric acid. The reaction was monitored by TLC. After consumption of the starting material the reaction mixture was diluted with 300 ml of ethyl acetate and was washed with 3×100 ml of 1N NaOH followed by brine (1×100 ml). The solution was dried over MgSO$_4$. Filtered and was concentrated in vacuo to provide 8.9 g of (L)-4-(2',6'-dimethoxyphenyl)phenylalanine, t-butyl ester. 500 MHz $^1$H NMR (CD$_3$OD): δ1.45 (s, 9H), 3.20 (d, 2H); 3.69 (s, 6H); 4.20 (t, 1H); 6.72 (d, 2H), 7.15 (m, 5H).

Reference Example 6
3(R)-amino-3-(4-biphenyl)propionic Acid, Methyl Ester
Step A
N-tert-Butoxycarbonyl-(S)-4-hydroxyphenylglycine To a solution of (S)-(4-hydroxyphenyl)glycine (Sigma Chemical) (6.5 g, 39 mmol) in dioxane/water (1:1, 120 mL) was added triethylamine (5,9 g, 8.2 mL, 58 mmol) and [2-(tert-butoxycarbonyloxyimino)-2-phenylacetonitrile] (BOC-ON; 11 g, 45 mmol). After stirring overnight at room temperature, 300 mL of brine was added to the solution and the mixture was extracted with ether. (3×100 mL). The aqueous layer was acidified with HCl (pH=2) and extracted with 3×100 mL of ethyl acetate. The ethyl acetate layer was dried over MgSO$_4$, filtered and the solvent removed under reduced pressure. The residue was chromatographed with 98/2 to 95/5 methylene chloride/methanol. Recovered 12 g of crude product. The impurity was removed following esterification of the product in the next step.

400 MHz $^1$H NMR (CDCl$_3$): δ1.37 (s, 9), 5.1 (1H, br s), 6.7 (d, 2H, J=8 Hz), 7.15 (d, 2H, J=8 Hz).
Step B
N-tert-Butoxycarbonyl-(S)-4-hydroxyphenylglycine, Methyl Ester In a 50 mL round bottomed flask was added a 1:1 mixture of benzene:methanol and N-tert-butoxycarbonyl-(S)-4-hydroxyphenylglycine (2.8 g, 11 mmol). The solution was cooled to 0° C. and a 2 M solution of trimethylsilyldiazomethane (Aldrich Chemical Co.) in hexane was added with vigorous stirring until a slight yellow color persisted. Then the reaction mixture solvents were removed under reduced pressure and the crude product was purified by flash chromatography (80/20 hexane/ethyl acetate) to give N-tert-butyloxycarbonyl-(S)-4-hydroxyphenylglycine, methyl ester (2.05 g, 7.3 mmol) (66% yield).

300 MHz $^1$H NMR (CDCl$_3$): δ1.43 (s, 9H), 3.71 (s, 3H), 5.22 (br d, 1H), 5.57 (1H, br d), 5.80 (br s, 1H), (6.7 (d, 2H, J=8 Hz), 7.17 (d, 2H, J=8 Hz).
step C
N-tert-Butoxycarbonyl-(S)-4-(trifluoromethylsulfonyloxy) phenylglycine, Methyl Ester To a 25 mL round bottom flask fitted with a stir bar and septum was added N-tert-butyloxycarbonyl-(S)-4-hydroxyphenylglycine, methyl ester (1.9 g, 6.8 mmol) and pyridine (2.8 mL, 33 mmol) in 12 mL of methylene chloride. The flask was purged with N$_2$, cooled to 0° and trifluoromethanesulfonic anhydride (1.38 mL, 7.8 mmol) was added dropwise over several minutes, keeping the temperature at or below 4° C. The solution was stirred for 1 h, then at room temperature for 4 h. The mixture was diluted with 20 mL of methylene chloride. The mixture was washed with 20 mL of 0.5 N NaOH, 1×20 mL of water and 2×20 mL of 10% citric acid. Dry the organic layer over MgSO$_4$, filter, reduce the volume. Flash chromatography (75/25 hexane/methylene chloride) gave 2.3 g of desired product (81% yield).

300 MHz $^1$H NMR (CDCl$_3$): δ1.43 (s, 9H), 3.74 (s, 3H), 5.35 (1H, br d), 5.68 (br s, 1H), 7.27 (d, 2H, J=8 Hz), 7.47 (d, 2H, J=8 Hz).
Step D
N-tert-Butoxycarbonyl-(S)-(4-biphenyl)glycine To a 25 mL round bottom flask fitted with a stir bar and septum was added N-tert-butyloxycarbonyl-(S)-4-trifluoromethylsulfonyloxyphenylglycine, methyl ester (690 mg, 1.67 mmol), anhydrous potassium carbonate (348 mg, 2.6 mmol) and benzeneboronic acid (411 mg, 3.4 mmol) in 15 ml of toluene and 3 mL of ethanol. The mixture was degassed under nitrogen with three freeze-thaw cycles and tetrakis(triphenylphosphine) palladium (94 mg, 0.085 mmol) was added to the reaction mixture and the mixture was heated between 75–90° C. for 4 h. The solvent was removed under reduced pressure and the residue flash chromatographed with 85/15 hexane/ethyl acetate. Recovered 600 mg of the methyl ester (quantitative yield).

300 MHz $^1$H NMR (CDCl$_3$): δ1.44 (s, 9H), 3.75 (s, 3H), 5.37 (1H, br d), 5.62 (br s, 1H), 7.36 (m,.1H), 7.45 (m, 4H), 7.57 (m, 4H).

The ester was hydrolyzed with 1.2 eq of KOH in 10 mL of 4:1 ethanol:water (2 h). The solution was acidified with 2 N HCl (pH=2). Remove the solvents in vacuo and extract the free acid with methylene chloride. Recovered 430 mg of free acid (66% yield).
Step E
3-(N-tert-Butyloxycarbonyl)amino-1-diazo-3-(4-biphenyl) propan-2-one To a 25 mL round bottom flask fitted with a stir bar and septum was added N-tert-butoxycarbonyl-(S)-4-biphenylglycine (430 mg, 1.31 mmol) in 10 mL of 2:1 methylene chloride:ether. The mixture was cooled to 0° C. and N-methylmorpholine (159 μl, 1.44 mmol) was added, followed by dropwise addition of isobutylchloroformate (179 □1, 1.38 mmol). The mixture was stirred for 1 h at 0° C., then diazomethane in ether (excess, prepared from Diazald^R by literature procedure) was added dropwise to the reaction mixture. The mixture was stirred for 1 h then quenched with saturated sodium bicarbonate. The mixture was extracted with ethyl acetate. (2×5 mL), washed with brine then dried over $MgSO_4$. The mixture was filtered, the solvent removed under reduced pressure and the product isolated by flash chromatography (80/20 hexane/ethyl acetate) to give 280 mg (0.78 mmol) of product (58% yield).

300 MHz $^1$H NMR ($CDCl_3$): δ1.42 (s, 9H), 5.22 (bs, 1H), 5.29 (s, 1H), 5.9 (br s, 1H), 7.35–7.5 (m, 5H), 7.52–7.62 (m, 4H).

Step F

3(R)-amino-3-(4-biphenyl)propionic Acid, Methyl Ester

To a 25 mL round bottom flask fitted with a stir bar and septum was added (3-diazo-2-oxopropyl-1-(S)-(4-biphenyl))carbamic acid,tert-butyl ester (280 mg, 0.76 mmol), with 5 mL each of methanol and dioxane. The flask was cooled to 0° C. and 0.15 eq (34 mg, 0.038 mmol) of silver benzoate in 500 μl of triethylamine was added dropwise to the reaction mixture and the mixture allowed to stir at 25° C. for 1 h. The reaction was worked up with 10% $NH_4OH$ in saturated $NH_4Cl$ (10 mL). Extract with ether (3×10 mL) and dry the organic layer over $MgSO_4$. Filter, reduce the volume and flash chromatograph with 85/15 hexane/ethyl acetate. Recovered 260 mg of product (98% yield). Take this material and dissolve it in 10 mL of 1 N HCl in ethyl acetate. After stirring 2 h at room temperature, we obtained 180 mg of 3(R)-amino-(4-biphenyl)propionic acid, methyl ester hydrochloride. 300 MHz $^1$H NMR ($CD_3OD$): δ2.90 (dd, 1H, J=18 Hz, J=6 Hz), 3.02 (dd, 1H, J=18 Hz, J=6 Hz), 3.66 (s, 3H), 5.9 (br s, 1H), 7.33–7.5 (m, 5H), 7.55–7.6 (m, 4H).

The following 3(R)-amino-propionic acid derivatives were prepared by the procedures described in Reference Example 6 substituting the appropriate boronic acid analog for benzeneboronic acid:

3(R)-amino-3-(4-(2'-methoxyphenyl)phenyl)propionic acid, methyl ester;

3(R)-amino-3-(4-(2',6'-dimethoxyphenyl)phenyl)propionic acid, methyl ester.

The following examples are provided to illustrate the invention and are not to be construed as limiting its scope in any manner.

EXAMPLE 1

N-(pyrrolidine-1-carbonyl)-(L)-4-(2'-methoxyphenyl) phenylalanine

To a solution of 0.05 g (0.14 mmol) of L-2-(methoxyphenyl)phenylalanine t-butyl ester in 1 ml of methylene chloride was added 0.14 (mmol) of diisopropyl ethyl amine at 0° C. To this solution was added 27.5 mg of p-nitro-chloroformate as a solid. After 30 minutes a cocktail of 13 mg (0.19 mmol) of pyrrolidine and 0.05 g (0.4 mmol) of diisopropyl ethyl amine was added. The yellow solution was stirred for 2 hours at room temperature. The solution was diluted with ethyl acetate and was washed with 5% citric acid solution (3×5 ml), saturated $NaHCO_3$ solution (2×5 ml) and water and brine (1×5 ml and was dried over $MgSO_4$. The product was purified by preparatory thin layer chromatography over silica gel eluting with 50% EtOAc/hexanes. The t-butyl ester was removed by treatment with 50% TFA/CH2Cl2 for one hour followed by concentration in vacuo. The product was purified by preparatory thin layer chromatography eluting with 5% MeOH/CH2Cl2/1% HOAc to give the desired product. 300 MHz $^1$H NMR ($CD_3OD$): δ1.89 (m, 4H); 3.05 (dd, 1H); 3.20–3.40 (5H); 3.79 (s, 3H); 4.57 (dd, 1H); 6.95–7.05 (m, 2H); 7.20–7.30 (m, 4H); 7.40 (d, 2H). MS: Obs. 583 ($M^+$+1).

GENERAL PROCEDURE FOR THE SOLID-PHASE SYNTHESIS OF COMPOUNDS OF FORMULA 1

Described below is the method used for preparing N-FMOC-(L)-2'-cyano-biphenylalanine resin. Application of the identical method to the amino acids described in Examples 2–6 provided the appropriate resins for preparation of the examples prepared via solid phase chemistry. Some commercially available N-FMOC-amino acid resins were also utilized. All reactions were carried out in polyethylene syringes fitted with frits (Applied Seperations) and capped with adaptors (Varian) and teflon stopcocks (Jones Chromatography). Agitation of the vessels was performed by rotation on a tube rotator.

Step A

Loading of N-FMOC-(L)-4-(2'-cyanophenyl)phenylalanine Onto Resin 5.0 g (4.75 mmol based on 0.95 mmol/g capacity) of Wang resin (Bachem) was suspended in 60 ml of 50% $THF/CH_2Cl_2$ (sufficient to ensure semi-fluid state) and treated with 4.64 g (9.5 mmol) N-FMOC-(L)-4-(2'-cyanophenyl)phenylalanine, 1.81 g (9.5 mmol) of EDC and 0.63 g (4.7 mmol) of DMAP. The mixture was agitated for 2.5 hours and filtered through the integral frit. The resin was washed twice with 50% $THF/CH_2Cl_2$ (50 ml) and the reaction was repeated as above. The mixture was filtered though the integral frit and washed: $THF/CH_2Cl_2$ (3×50 ml), $CH_2Cl_2$ (2×50 ml), MeOH (2×50 ml), $CH_2Cl_2$ (50 ml), MeOH (50 ml), $CH_2Cl_2$ (2×50 ml) and ether (2×50 ml). The resin was dried in vacuo to give 7.20 g of the desired product.

Loading was evaluated by treating 50 mg of the resin in a 2 ml polyethylene syringe with 95% $TFA/H_2O$ (3×2 ml for 10 minutes). The combined filtrates were concentrated in vacuo and the residue was weighed and analyzed by HPLC, NMR. The loading of the resin from Step A was 0.78 mmol/g and the recovered amino acid was >90% pure by HPLC (210 nM).

Step B

Deprotection of the FMOC Group 50 mg (0.047 mmol based on 0.95 mmol/g loading) of the resin from Step A was placed in a 2 ml polyethylene frit fitted syringe. The syringe outlet was capped by a teflon stopcock. The resin was treated with 2 ml (3×10 min) of 20% piperidine in DMF. Following the final treatment the resin was washed with DMF (3×2 ml) and 50% methylenechloride/THF (3×2 ml).

Step C

Preparation of Ureas

The resin from Step B (in the same reaction vessel) was treated with a solution made up in 1.5 ml DMF of 0.75 mmol of diisopropylethylamine and 0.75 mmol of p-nitrochloroformate. The vessel was capped with an adaptor and teflon stopcock and rotated for one hour. The reaction mixture was filtered and the resin was washed with 50% $CH_2Cl_2/THF$ (2×2 ml). 1.5 ml of a 0.5M solution of the amine and diisopropyl ethyl amine (2 equivalents of diisopropyl ethyl amine was added in the case of an amine salt) was added. The yellow suspension was rotated for 2 hours. A The resin was washed with DMF (3×2 ml) and $CH_2Cl_2$ (2×2 ml). A 1 mg aliquot of the resin was submitted to the Kaiser test to confirm that all primary amine had been acylated. If the conversion was complete the resin was washed:: DMF (3×2 ml), $CH_2Cl_2$ (2×2 ml), MeOH (2×2 ml), $CH_2Cl_2$ (2 ml), MeOH (2 ml), $CH_2Cl_2$ (3×2 ml).

Step D

Cleavage of the Product From the Resin

The resin (in the original vessel) was treated with 95% TFA/H$_2$O (3×1.5 ml) and the resulting filtrates were collected in a previously tared 13 mm×100 mm test tube. The filtrate was concentrated in vacuo in a rotory concentrator. The residue was dissolved in approximatly 3 ml of 30% CH$_3$CN/H$_2$O and aliquots were removed for H PLC and MS analysis. The solution was then lyophilized to provide the desired product. Criteria for assay included >80% purity by HPLC and structure was confirmed by mass spectrum.

The following Examples were prepared by the above-described method:

| Example | Compound Name | MS* |
|---|---|---|
| 2 | N-(2-benzyloxycarbonyl-pyrrolidine-1-carbonyl)-(L)-4-biphenylalanine | 474 |
| 3 | N-(2-methoxycarbonyl-pyrrolidine-1-carbonyl)-(L)-4-biphenylalanine | 397 |
| 4 | N-(2,5-dimethyl-pyrrolidine-1-carbonyl)-(L)-4-biphenyl-alanine | 367 |
| 5 | N-(pyrrolidine-1-carbonyl)-(L)-4-biphenylalanine | 339 |
| 6 | N-((2-tetrahydrofurryl)methylaminocarbonyl)-(L)-4-biphenylalanine | 369 |
| 7 | N-(2-(phenylaminomethyl)-pyrrolidine-1-carbonyl)-(L)-4-biphenylalanine | 444 |
| 8 | N-(2-(hydroxymethyl)-pyrrolidine-1-carbonyl)-(L)-4-biphenylalanine | 369 |
| 9 | N-(pyrrolidine-1-carbonyl)-(L)-4-(2'-cyanophenyl)-phenylalanine | 85% by HPLC |
| 10 | N-(2-methoxycarbonyl-pyrrolidine-1-carbonyl)-(L)-4-(2'-methoxyphenyl)phenylalanine | 79% by HPLC |
| 11 | N-(N-phenyl-aminocarbonyl)-(L)-4-(2'-cyanophenyl)-phenylalanine | 87% by HPLC Note 1 |
| 12 | N-(3-benzyl-3-ethoxylcarbonyl-piperidine-1-carbonyl)-(L)-4-(2'-cyanophenyl)phenylalanine (Isomer A) | 540 |
| 13 | N-(3-benzyl-3-ethoxylcarbonyl-piperidine-1-carbonyl)-(L)-4-(2'-cyanophenyl)phenylalanine (Isomer B) | 540 |
| 14 | N-(4-benzoyl-piperidine-1-carbonyl)-(L)-4-(2'-cyanophenyl)phenylalanine | 483 |
| 15 | N-(1-methylsulfonyl-indoline-3-spiro-4'-piperidine-1'-carbonyl)-(L)-4-(2'-cyanophenyl)phenylalanine | 559 |
| 16 | N-(4-cyano-4-phenyl-piperidine-1-carbonyl)-(L)-4-(2'-cyanophenyl)phenylalanine | 479 |
| 17 | N-(4-(2-(2-ethoxycarbonylethyl)phenyl-piperidine-1-carbonyl)-(L)-4-(2'-cyanophenyl)phenylalanine | 554 |
| 18 | N-(4-(2-methoxyphenyl)-piperazine-1-carbonyl)-(L)-4-(2'-cyanophenyl)phenylalanine trifluoroacetic acid salt | 485 |
| 19 | N-(3-benzyl-piperidine-1-carbonyl)-(L)-4-(2'-cyanophenyl)phenylalanine | 468 |
| 20 | N-(6,7-dimethoxy-1,2,3,4-tetrahydroisoquinoline-2-carbonyl)-(L)-4-(2'-cyanophenyl)phenylalanine | 486 |
| 21 | N-(3-dimethylaminocarbonyl-indan-1-spiro-4'-piperidine-1'-carbonyl)-(L)-4-(2'-cyanophenyl)-phenylalaine | 551 |
| 22 | N-(4-diphenylmethyl-piperazine-1-carbonyl)-(L)-4-(2'-cyanophenyl)phenylalanine trifluoroacetic acid salt | 545 |
| 23 | N-(4-(3,4-dioxomethylene-phenylmethyl)-piperazine-1-carbonyl)-(L)-4-(2'-cyanophenyl)phenylalanine trifluoroacetic acid salt | 513 |
| 24 | N-(indene-1-spiro-4'-piperidine-1'-carbonyl)-(L)-4-(2'-cyanophenyl)phenylalanine | 478 |
| 25 | N-(4-(2-chlorobenzoyl)-piperidine-1-carbonyl)-(L)-4-(2'-cyanophenyl)phenylalanine | 516 |
| 26 | N-(4-aminocarbonyl-4-phenyl-piperidine-1-carbonyl)-(L)-4-(2'-cyanophenyl)phenylalanine | 497 |
| 27 | N-(4-benzyl-piperidine-1-carbonyl)-(L)-4-(2'-cyanophenyl)phenylalanine | 468 |
| 28 | N-(3-ethoxycarbonyl-indan-1-spiro-4'-piperidine-1'-carbonyl)-(L)-4-(2'-cyanophenyl)phenylalanine | 552 |
| 29 | N-(morpholine-4-carbonyl)-(L)-4-(2'-cyanophenyl)-phenylalanine | 380 |
| 30 | N-(4-ethoxycarbonyl-piperidine-1-carbonyl)-(L)-4-(2'-cyanophenyl)phenylalanine | 450 |
| 31 | N-(4-benzyl-piperazine-1-carbonyl)-(L)-4-(2'-cyanophenyl)phenylalanine trifluoroacetic acid salt | 469 |
| 32 | N-(4-(2-chlorophenyl)-piperazine-1-carbonyl)-(L)-4-(2'-cyanophenyl)phenylalanine trifluoroacetic acid salt | 489 |
| 33 | N-(N-(3-(6,7-benzo-2-oxo-azacycloheptane)-aminocarbonyl)-(L)-4-(2'-cyanophenyl)phenylalanine | 469 |
| 34 | N-(N-methyl-N-phenyl-aminocarbonyl)-(L)-4-(2'-cyanophenyl)phenylalanine | 400 |
| 35 | N-(piperidine-1-carbonyl)-(L)-4-(2'-cyanophenyl)-phenylalanine | 378 |
| 36 | N-(N,N-diethyl-aminocarbonyl)-(L)-4-(2'-cyanophenyl)-phenylalanine | 366 |
| 37 | N-(N,N-diethyl-aminocarbonyl)-(L)-4-(2'-methoxyphenyl)phenylalanine | 371 |
| 38 | N-(1-methylsulfonyl-indoline-3-spiro-4'-piperidine-1'-carbonyl)-(L)-4-(2'-methoxyphenyl)phenylalanine | 564 |
| 39 | N-(4-benzoyl-piperidine-1-carbonyl)-(L)-4-(2'-methoxyphenyl)phenylalanine | 486 M$^+$ |
| 40 | N-(morpholine-4-carbonyl)-(L)-4-(2'-methoxyphenyl)-phenylalanine | 385 |
| 41 | N-(4-(3,4-dioxomethylene-phenylmethyl)-piperazine-1-carbonyl)-(L)-4-(2'-methoxyphenyl)phenylalanine trifluoroacetic acid salt | 518 |
| 42 | N-(4-(2-furoyl)-piperazine-1-carbonyl)-(L)-4-(2'-methoxyphenyl)phenylalanine | 478 |
| 43 | N-(N-(3-(6,7-benzo-2-oxo-azacycloheptane)aminocarbonyl)-(L)-4-(2'-methoxyphenyl)phenylalanine; | 474 |
| 44 | N-(3-ethoxycarbonyl-indan-1-spiro-4'-piperidine-1'-carbonyl)-(L)-4-(2'-methoxyphenyl)phenylalanine | 557 |

MS*: mass spectrum, m/e = (M)$^+$ or (M + 1(H$^+$))$^+$ or (M + 18 (NH$_4^+$))$^+$.

GENERAL PROCEDURE FOR THE SOLUTION-PHASE SYNTHESIS OF COMPOUNDS OF FORMULA 1 BY REACTION WITH ISOCYANATES 2,6-(Dimethoxyphenyl)phenylalanine t-butyl ester hydrochloride (20 mg, 0.05 mmol) was combined with 1 mmol of triethyl amine and 1 mmol of the isocyanate in 1.5 ml of methylene chloride. The solution was agitated over night. 100 mg of tris(2-aminoethyl)amine polymer bond resin was added and the mixture was agitated over night. The mixture was filtered through 2 grams of Varian SCX resin and 1 gram of neutral alumina and eluted with ether into a 10 ml test tube. The tubes were concentrated in vacuo and the residue was treated with 50% TFA/CH$_2$Cl$_2$ for one hour and concentrated in vacuo. The residue was lyophilized from 50% acetonitrile water to provide the following compounds of Formula 1.

The following Examples were prepared by the above described method:

| Example | Compound Name | MS* |
|---|---|---|
| 45 | N-(N-(3-methoxyphenyl)-aminocarbonyl)-(L)-4-(2',6'-dimethoxyphenyl)phenylalanine | 451 |
| 46 | N-(N-(3-methylphenyl)-aminocarbonyl)-(L)-4-(2',6'-dimethoxyphenyl)phenylalanine | 435 |
| 47 | N-(N-(4-fluorophenyl)-aminocarbonyl)-(L)-4-(2',6'-dimethoxyphenyl)phenylalanine | 439 |
| 48 | N-(N-phenyl-aminocarbonyl)-(L)-4-(2',6'-dimethoxy-phenyl)phenylalanine | 421 |
| 49 | N-(N-benzyl-aminocarbonyl)-(L)-4-(2',6'-dimethoxy-phenyl)phenylalanine | 435 |

-continued

| Example | Compound Name | MS* |
|---|---|---|
| 50 | N-(N-cyclohexyl-aminocarbonyl)-(L)-4-(2',6'-dimethoxyphenyl)phenylalanine | 427 |
| 51 | N-(N-(1-(1-naphthyl)ethyl)-aminocarbonyl)-(L)-4-(2',6'-dimethoxyphenyl)phenylalanine | 499 |
| 52 | N-(N-(2-methoxycarbonylphenyl)-aminocarbonyl)-(L)-4-(2',6'-dimethoxyphenyl)phenylalanine | 479 |
| 53 | N-(N-(3,5-di(trifluoromethyl)phenyl)-aminocarbonyl)-(L)-4-(2',6'-dimethoxyphenyl)phenylalanine | 557 |
| 54 | N-(N-(3,5-dichlorophenyl)-aminocarbonyl)-(L)-4-(2',6'-dimethoxyphenyl)phenylalanine | 490 |
| 55 | N-(N-(4-ethoxycarbonylphenyl)-aminocarbonyl)-(L)-4-(2',6'-dimethoxyphenyl)phenylalanine | 493 |
| 56 | N-(N-(2-methoxyphenyl)-aminocarbonyl)-(L)-4-(2',6'-dimethoxyphenyl)phenylalanine | 451 |
| 57 | N-(N-(2-methylphenyl)-aminocarbonyl)-(L)-4-(2',6'-dimethoxyphenyl)phenylalanine | 435 |
| 58 | N-(N-(2,6-dichlorophenyl)-aminocarbonyl)-(L)-4-(2',6'-dimethoxyphenyl)phenylalanine | 489 |

MS*: mass spectrum, m/e = $(M)^+$ or $(M + 1(H^+))^+$ or $(M + 18 (NH_4^+))^+$.

GENERAL PROCEDURE FOR THE SOLUTION-PHASE SYNTHESIS OF COMPOUNDS OF FORMULA 1 BY REACTION WITH P-NITROPHENYL CHLOROFORMATE AND AN AMINE 2,6-(Dimethoxyphenyl)phenylalanine t-butyl ester (0.3 g, 0.76 mmol) was suspended in 10 ml of methylene chloride to which 0.13 g (1.6 mmol) of pyridine had been added at 0° C. To this mixture was added 0.15 g (0.76 mmol) of p-nitrophenyl chloroformate. The solution was warmed to room temperature and stirred until the solid had dissolved (reaction is faster if the amino acid free base is utilized). The solution was diluted with ethyl acetate and was washed with 1N HCl (3×10 ml) and brine (1×10 ml) and was dried over $MgSO_4$. The mixture was filtered and concentrated in vacuo. The residue (0.39 g) was re-dissolved in 10 ml of methylene chloride and distributed equally into 10 teflon capped vials into which 0.3 mmol of the amine of which the urea is to be made had been added. In cases where an immediate yellow color did not form 0.2 mmol of diidopropyl ethyl amine was added to form the intermediate amino acid isocyanate. The vails were left to age over night. The crude products were isolated and purified by automated medium pressure chromatography over 10 grams of silica gel eluting with a gradient of 10–100% ethyl acetate/hexanes over 10 minutes followed by 100% EtOAc for 10 minutes. The recovered products were treated with 50% TFA/CH2Cl2 for one hour and concentrated in vacuo to provide the desired compounds of Formula 1.

| Example | Compound Name | MS* |
|---|---|---|
| 59 | N-(indan-1-spiro-4'-piperidine-1'-carbonyl)-(L)-4-(2'-methoxyphenyl)phenylalanine | >80% by HPLC |
| 60 | N-(morpholine-4-carbonyl)-(L)-4-(2',6'-dimethoxyphenyl)-phenylalanine | 415 |
| 61 | N-(piperidine-1-carbonyl)-(L)-4-(2',6'-dimethoxyphenyl)-phenylalanine | 413 |
| 62 | N-(4-methyl-piperidine-1-carbonyl)-(L)-4-(2',6'-dimethoxy-phenyl)phenylalanine | 427 |
| 63 | N-(3,4-dimethyl-piperidine-1-carbonyl)-(L)-4-(2',6'-dimethoxyphenyl)phenylalanine | 441 |

-continued

| Example | Compound Name | MS* |
|---|---|---|
| 64 | N-(3,5-dimethyl-piperidine-1-carbonyl)-(L)-4-(2',6'-dimethoxyphenyl)phenylalanine | 441 |
| 65 | N-(azacycloheptane-1-carbonyl)-(L)-4-(2',6'-dimethoxy-phenyl)phenylalanine | 427 |
| 66 | N-(4-benzyl-piperidine-1-carbonyl)-(L)-4-(2',6'-dimethoxy-phenyl)phenylalanine | 503 |
| 67 | N-(2-ethoxycarbonyl-piperidine-1-carbonyl)-(L)-4-(2',6'-dimethoxyphenyl)phenylalanine | 485 |
| 68 | N-(2-methyl-piperidine-1-carbonyl)-(L)-4-(2',6'-dimethoxy-phenyl)phenylalanine | 427 |
| 69 | N-(2-hydroxymethyl-pyrrolidine-1-carbonyl)-(L)-4-(2',6'-dimethoxyphenyl)phenylalanine | 429 |
| 70 | N-(3-ethoxycarbonyl-piperidine-1-carbonyl)-(L)-4-(2',6'-dimethoxyphenyl)phenylalanine | 485 |
| 71 | N-(3-methyl-piperidine-1-carbonyl)-(L)-4-(2',6'-dimethoxyphenyl)phenylalanine | 427 |
| 72 | N-(4-(1-piperidinyl)-piperidine-1-carbonyl)-(L)-4-(2',6'-dimethoxyphenyl)phenylalanine trifluoroacetic acid salt | 498 |
| 73 | N-(4,6,6-trimethyl-[3.2.1]-2-azabicyclo-octane-2-carbonyl)-(L)-4-(2',6'-dimethoxyphenyl)phenylalanine | 481 |
| 74 | N-(2-methyl-7-fluoro-1,2,3,4-tetrahydroquinoline-1-carbonyl)-(L)-4-(2',6'-dimethoxyphenyl)phenylalanine | 495 |
| 75 | N-(1,2,3,4-tetrahydroquinoline-1-carbonyl)-(L)-4-(2',6'-dimethoxyphenyl)phenylalanine | 461 |
| 76 | N-(2,6-dimethyl-piperidine-1-carbonyl)-(L)-4-(2',6'-dimethoxyphenyl)phenylalanine | 442 |
| 77 | N-(4-(4-methyl-piperazine-1-carbonyl)-(L)-4-(2',6'-dimethoxyphenyl)phenylalanine | 429 |
| 78 | N-(4-(3-benzyl-piperidine-1-carbonyl)-(L)-4-(2',6'-dimethoxyphenyl)phenylalanine | 540 |
| 79 | N-(4-(4-phenyl-piperazine-1-carbonyl)-(L)-4-(2',6'-dimethoxyphenyl)phenylalanine | 491 |
| 80 | N-(N-n-hexyl-N-methyl-aminocarbonyl)-(L)-4-(2',6'-dimethoxyphenyl)phenylalanine | 444 |
| 81 | N-(4-(thiamorpholine-4-carbonyl)-(L)-4-(2',6'-dimethoxyphenyl)phenylalanine | 432 |
| 82 | N-(N-methyl-N-phenyl-aminocarbonyl)-(L)-4-(2',6'-dimethoxyphenyl)phenylalanine | 436 |

MS*: mass spectrum, m/e = $(M)^+$ or $(M + 1(H^+))^+$ or $(M + 18 (NH_4^+))^+$.

Note 1: Prepared by treatment of FMOC deprotected resin with phenyl isocyanate in 50% $CH_2Cl_2$/THF.

EXAMPLE 83

Inhibition of VLA-4 Dependent Adhesion to BSA-CS-1 Conjugate

Step A

Preparation of CS-1 Coated Plates

Untreated 96 well polystyrene flat bottom plates were coated with bovine serum albumin (BSA; 20 mg/ml) for 2 hours at room temperature and washed twice with phosphate buffered saline (PBS). The albumin coating was next derivatized with 10 mg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 mg/ml and allowed to react for 2 hours at room temperature. The plates were washed twice with PBS and stored at 4° C.

Step B

Preparation of Fluorescently Labeled Jurkat Cells

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 mg/ml streptomycin and 2 mM glutamine.

Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of $2 \times 10^6$ cells/ml in PBS containing a 1 mM concentration of a fluorogenic esterase substrate (2', 7'-bis-(2-carboxyethyl)-5-(and -6)carboxyfluorescein, acetoxymethyl ester; BCECF-AM; Molecular Probes Inc., Eugene, Oreg.; catalog #B-1150) for 30–60 minutes at 37° C. in a 5% $CO_2$/air incubator. The fluorescently labeled Jurkat cells were washed two times in PBS and resuspended in RPMI containing 0.25% BSA at a final concentration of $2.0 \times 10^6$ cells/ml.

Step C
Assay Procedure

Compounds of this invention were prepared in DMSO at 100× the desired final assay concentration. Final concentrations were selected from a range between 0.001 nM–100 mM. Three mL of diluted compound, or vehicle alone, were premixed with 300 mL of cell suspension in 96-well polystyrene plates with round bottom wells. 100 mL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 84
Antagonism of VLA-4 Dependent Binding to VCAM-Ig Fusion Protein
Step A
Preparation of VCAM-Ig The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3'; 5'-PCR primer: 5'-ATAGGAATTCCAGCTGCCACCATGCCTGGGAAG ATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1: MPGKMVVILGASNILWIM-FAASQAFKIETTPESRYLAQIGDSVSLTCSTTGCES PFFSWRTQIDSPLNGKVTNEGTTSTLTM-NPVSFGNEHSYLCTATCESRKLEKGI QVEIYSFPKD-PEIHLSGPLEAGKPITVKCSVAD-VYPFDRLEIDLLKGDHLMKSQ EFLEDADRKSLETKSLEVTFT-PVIEDIGKVLVCRAKLHIDEMDSVPTVRQAVK EL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL661) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 mg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B
Preparation of $^{125}$I-VCAM-Ig

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C
VCAM-Ig Binding Assay

Compounds of this invention were prepared in DMSO at 100× the desired final assay concentration. Final concentrations were selected from a range between 0.001 nM–100 μM. Jurkat cells were centrifuged at 400× g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM $MnCl_2$; (ii) 20 μL of $^{125}$I-VCAM-Ig in binding buffer containing 1 mM $MnCl_2$ (final assay concentration ~100 pM); (iii) 2.5 μL of compound solution or DMSO; (iv) and $0.5 \times 10^6$ cells in a volume of 30 mL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Contol wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the IC$_{50}$ was determined from a ten point titration using a validated four parameter fit algorithm.

EXAMPLE 85

Antagonism of $\alpha_1\beta_7$ Dependent Binding to VCAM-Ig Fusion Protein

Step A $\alpha_1\beta_7$ Cell Line

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 penicillin/100 μg streptomycin/2 mM L-glutamine at 37° C., 5% carbon dioxide. The cells were pelleted at 1000 rpm for 5 minutes and then washed twice and resuspended in binding buffer (25 mM Hepes, 150 mM NaCl, 0.1% BSA, 3 mM KCl, 2 mM Glucose, pH 7.4).

Step B

VCAM-Ig Binding Assay

Compounds of this invention were prepared in DMSO at 100× the desired final assay concentration. Final concentrations were selected from a range between 0.001 nM–100 μM. Compounds were assayed in Millipore MHVB multi-screen plates (Cat# MHVBN4550) by making the following sequential additions to duplicate wells: (i) 100 ml/well of binding buffer containing 1.5 mM MnCl$_2$; (ii) 10 ml/well $^{125}$I-VCAM-Ig in binding buffer (final assay concentration <500 pM); (iii) 1.5 ml/well test compound or DMSO alone; (iv) 38 ml/well RPMI-8866 cell suspension (1.25×10$^6$ cells/well). The plates were incubated at room temperature for 45 minutes on a plate shaker at 200 rpm, filtered on a vacuum box, and washed on the same apparatus by the addition of 100 mL of binding buffer containing 1 mM MnCl$_2$. After insertion of the multiscreen plates into adapter plates (Packard, Meriden, Conn., cat# 6005178), 100 mL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the IC$_{50}$ was determined from a ten point titration using a validated four parameter fit algorithm.

What is claimed is:

1. A compound having the formula I:

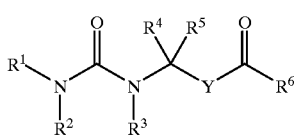

or a pharmaceutically acceptable salt thereof wherein:

R$^1$ and R$^2$ together with the nitrogen to which they are attached form a monocyclic heterocycle having 4 to 7 members and containing 0–2 additional heteroatoms independently selected from oxygen, sulfur and nitrogen, with the proviso that when the additional heteroatom is nitrogen, it is not adjacent to the urea nitrogen atom; said heterocycle being optionally substituted with one to four groups selected from phenyl optionally substituted with halogen or C$_{1-3}$alkoxy, benzyl, C$_{1-5}$alkyl optionally substituted with hydroxy or NR$^f$Rg, CO$_2$R$^d$, C(O)R$^d$, and C(O)NR$^d$R$^e$; said heterocycle further being optionally (1) fused to a benzene ring or (2) spiro-fused to a 5- or 6-membered saturated or unsaturated ring optionally containing one heteroatom selected from O, S, and N and optionally fused to a benzene ring; wherein said benzene and spiro-fused ring are each optionally substituted with one to four groups selected from R$^b$;

R$^3$ is
1) hydrogen,
2) C$_{1-10}$alkyl,
3) C$_{2-10}$-alkenyl,
4) C$_{2-10}$alkynyl
5) cycloalkyl,
6) heterocyclyl,
7) aryl,
8) heteroaryl,
wherein alkyl, alkenyl, alkynyl, cycloalkyl and heterocyclyl are optionally substituted with one to four substituents selected from R$^a$, and aryl and heteroaryl are optionally substituted with one to four substituents independently selected from R$^b$;

R$^4$ is biphenylmethyl optionally substituted with one or two groups selected from R$^b$;

R$^5$ is hydrogen;

R$^6$ is OH;

R$^a$ is
1) hydrogen,
2) —OR$^d$,
3) —NO$_2$,
4) halogen
5) —S(O)$_m$R$^d$,
6) —SR$^d$,
7) —S(O)$_2$OR$^d$,
8) —S(O)$_m$NR$^d$R$^e$,
9) —NR$^d$R$^e$,
10) —O(CR$^f$R$^g$)$_n$NR$^d$R$^e$,
11) —C(O)R$^d$,
12) —CO$_2$R$^d$,
13) —CO$_2$(CR$^f$R$^g$)$_n$CONR$^d$R$^e$,
14) —OC(O)R$^d$,
15) —CN,
16) —C(O)NR$^d$R$^e$,
17) —NR$^d$C(O)R$^e$,
18) —OC(O)NR$^d$R$^e$,
19) —NR$^d$C(O)OR$^e$,
20) —NR$^d$C(O)NR$^d$R$^e$,
21) —CR$^d$(N—OR$^e$),
22) CF$_3$; or
23) —OCF$_3$;

R$^b$ is
1) a group selected from R$^a$,
2) C$_{1-10}$alkyl,
3) C$_{2-10}$alkenyl,
4) C$_{2-10}$alkynyl,
5) Cy;
6) Cy–C$_{1-10}$alkyl,
wherein alkyl, alkenyl, alkynyl, and Cy are optionally substituted with one to four substituents selected from a group independently selected from R$^c$;

$R^c$ is
1) halogen,
2) $NR^fR^g$,
3) carboxy,
4) $C_{1-4}$alkyl optionally substituted with $C(O)O-C_{1-4}$alkoxy,
5) $C_{1-4}$alkoxy,
6) aryl,
7) aryl $C_{1-4}$alkyl,
8) hydroxy,
9) $CF_3$, or
10) aryloxy; or two $R^c$ groups on adjacent atoms of a benzene ring together form methylenedioxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0–2 additional heteroatoms independently selected from oxygen, sulfur and nitrogen;

$R^f$ and $R^g$ are independently selected from hydrogen, $C_{1-10}$alkyl, Cy and Cy-$C_{1-10}$alkyl; or $R^f$ and $R^g$ together with the carbon to which they are attached form a ring of 5 to 7 members containing 0–2 heteroatoms independently selected from oxygen, sulfur and nitrogen;

Cy is independently selected from cycloalkyl, heterocyclyl, aryl, or heteroaryl;

m is an integer from 1 to 2;

n is an integer from 1 to 10;

Y is a bond.

2. A compound selected from

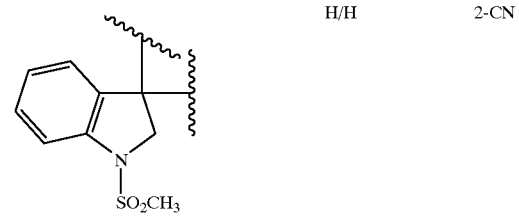

| $R^{b1}$ | $R^{b2}$ | $R^{b3}$ |
|---|---|---|
| H | PhCH$_2$OC(O) | H |
| H | CH$_3$OC(O) | H |
| CH$_3$ | CH$_3$ | H |
| H | H | H |
| H | PhNHCH$_2$ | H |
| H | OHCH$_2$ | H |
| H | H | 2-CN |
| H | CH$_3$OC(O) | 2-CH$_3$O |
| H | OHCH$_2$ | 2,6-diCH$_3$O |

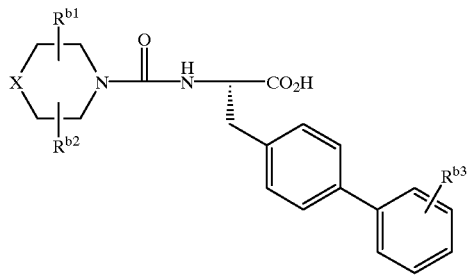

| X | $R^{b1}/R^{b2}$ | $R^{b3}$ |
|---|---|---|
| CH$_2$ | 3-PhCH$_2$/3-(CH$_3$CH$_2$OC(O)) | 2-CN |
| PhC(O)CH | H/H | 2-CN |
| [indoline-SO$_2$CH$_3$ group] | H/H | 2-CN |
| (CN)(Ph)C | H/H | 2-CN |
| 2-(CH$_3$CH$_2$OC(O)CH$_2$CH$_2$)—Ph—CN | H/H | 2-CN |
| (2-CH$_3$OPh)—N | H/H | 2-CN |
| CH$_2$ | H/3-PhCH$_2$ | 2-CN |
| [indane-C(O)N(CH$_3$)$_2$ group] | H/H | 2-CN |
| (Ph$_2$CH)N | H/H | 2-CN |
| [benzodioxole-CH$_2$N group] | H/H | 2-CN |
| [indene group] | H/H | 2-CN |
| 2-ClPhC(O)CH | H/H | 2-CN |
| (Ph)(NH$_2$C(O))C | H/H | 2-CN |
| PhCH$_2$CH | H/H | 2-CN |

-continued

| | | |
|---|---|---|
| [indanyl-C(O)OCH₂CH₃ structure] | H/H | 2-CN |
| O | H/H | 2-CN |
| CH₃CH₂OC(O)CH | H/H | 2-CN |
| PhCH₂N | H/H | 2-CN |
| (2-ClPh)N | H/H | 2-CN |
| CH₂ | H/H | 2-CN |
| [indoline-SO₂CH₃ structure] | H/H | 2-CH₃O |
| PhC(O)CH | H/H | 2-CH₃O |
| O | H/H | 2-CH₃O |
| [benzodioxole-CH₂N structure] | H/H | 2-CH₃O |
| [furan-C(O)N structure] | H/H | 2-CH₃O |
| [indanyl-C(O)OCH₂CH₃ structure] | H/H | 2-CH₃O |
| [indanyl structure] | H/H | 2-CH₃O |
| O | H/H | 2,6-diCH₃O |
| CH₂ | H/H | 2,6-diCH₃O |
| CH₃CH | H/H | 2,6-diCH₃O |
| CH₃CH | H/3-CH₃ | 2,6-diCH₃O |
| CH₂ | 3-CH₃/5-CH₃ | 2,6-diCH₃O |
| CH₂CH₂ | H/H | 2,6-diCH₃O |
| PhCH₂CH | H/H | 2,6-diCH₃O |
| CH₃CH₂OC(O)CH | H/H | 2,6-diCH₃O |
| CH₂ | H/2-CH₃ | 2,6-diCH₃O |
| CH₂ | 3-(CH₃CH₂OC(O)) | 2,6-diCH₃O |
| CH₂ | H/3-CH₃ | 2,6-diCH₃O |
| (1-piperidinyl)CH | H/H | 2,6-diCH₃O |
| CH₂ | 2-CH₃/6-CH₃ | 2,6-diCH₃O |
| CH₃N | H/H | 2,6-diCH₃O |
| CH₂ | H/3-PhCH₂ | 2,6-diCH₃O |
| PhN | H/H | 2,6-diCH₃O |
| S | H/H | 2,6-diCH₃O |

[structure: R¹R²N-C(O)NH-CH(CO₂H)-CH₂-biphenyl-Rᵇ]

| R¹ | R² | Rᵇ |
|---|---|---|
| 2-tetrahydrofurylmethyl | H | H |
| Ph | H | 2-CN |
| Ph | CH₃ | 2-CN |
| CH₃ | CH₃ | 2-CN |
| CH₃ | CH₃ | 2-CH₃O |
| 3-(CH₃O)Ph | H | 2,6-diCH₃O |
| 3-(CH₃)Ph | H | 2,6-diCH₃O |
| 4-F—Ph | H | 2,6-diCH₃O |
| Ph | H | 2,6-diCH₃O |
| benzyl | H | 2,6-diCH₃O |
| cHex | H | 2,6-diCH₃O |
| 1-napthylethyl | H | 2,6-diCH₃O |
| 2-CH₃OC(O)Ph | H | 2,6-diCH₃O |
| 3,5-diCF₃—Ph | H | 2,6-diCH₃O |
| 3,5-diCl—Ph | H | 2,6-diCH₃O |
| 4-(CH₃CH₂OC(O))Ph | H | 2,6-diCH₃O |
| 2-CH₃O—Ph | H | 2,6-diCH₃O |
| 2-CH₃—Ph | H | 2,6-diCH₃O |
| 2,5-diCl—Ph | H | 2,6-diCH₃O |
| n-C₆H₁₃ | CH₃ | 2,6-diCH₃O |
| Ph | CH₃ | 2,6-diCH₃O |

[structure: 6,7-dimethoxy-tetrahydroisoquinoline-C(O)NH-CH(CO₂H)-CH₂-biphenyl-2'-CN],

[structure: Chiral, benzazepinone-NH-C(O)-NH-CH(CO₂H)-CH₂-biphenyl-2'-CN],

-continued

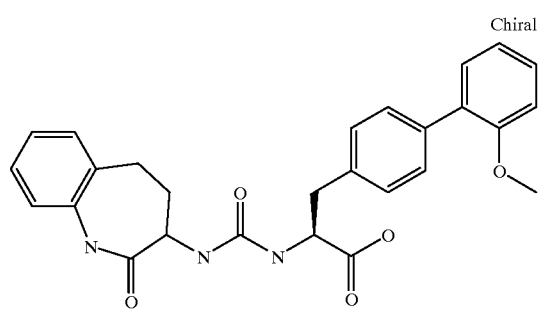

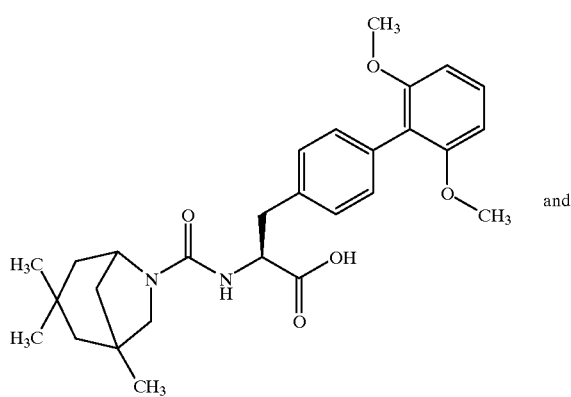 and

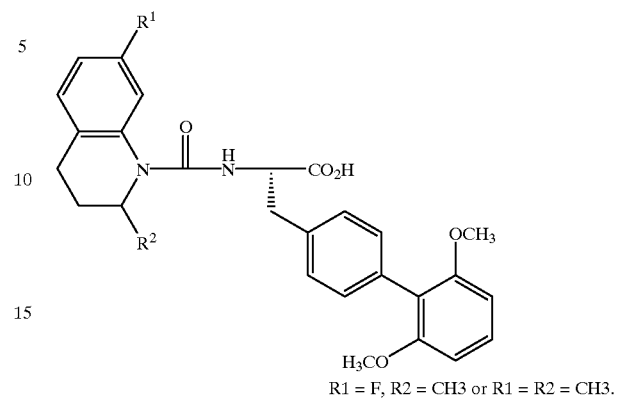

R1 = F, R2 = CH3 or R1 = R2 = CH3.

3. A compound of claim 1 wherein $R^3$ is hydrogen.

4. A compound of claim 1 wherein $R^4$ is biphenylmethyl substituted with one or two groups selected from $R^b$, and wherein one of the substituents is attached to the 2'-position.

5. A compound of claim 4 wherein $R^4$ is selected from 2'-cyanobiphenylmethyl, 2'-methoxy-biphenylmethyl and 2',6'-bis(methoxy)biphenylmethyl.

6. A method for the prevention or treatment of diseases, disorders, conditions or symptoms mediated by cell adhesion in a mammal which comprises administering to said mammal an effective amount of a compound of claim 1.

7. A pharmaceutical composition which comprises a compound of claim 1 and a pharmaceutically acceptable carrier.

* * * * *